(12) United States Patent
Ni et al.

(10) Patent No.: US 12,080,001 B2
(45) Date of Patent: Sep. 3, 2024

(54) SYSTEMS AND METHODS FOR OBJECT POSITIONING AND IMAGE-GUIDED SURGERY

(71) Applicant: SHANGHAI UNITED IMAGING HEALTHCARE CO., LTD., Shanghai (CN)

(72) Inventors: Cheng Ni, Shanghai (CN); Fei Gong, Shanghai (CN); Wei Zhang, Shanghai (CN); Yifeng Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 645 days.

(21) Appl. No.: 17/117,150

(22) Filed: Dec. 10, 2020

(65) Prior Publication Data
US 2021/0104055 A1    Apr. 8, 2021

Related U.S. Application Data

(63) Continuation of application No. PCT/CN2019/085021, filed on Apr. 29, 2019.

(51) Int. Cl.
*G06T 7/30* (2017.01)
*A61B 5/055* (2006.01)
(Continued)

(52) U.S. Cl.
CPC .............. *G06T 7/30* (2017.01); *A61B 5/055* (2013.01); *A61B 6/032* (2013.01); *A61B 6/0407* (2013.01);
(Continued)

(58) Field of Classification Search
CPC ... G06T 7/30; G06T 7/74; G06T 2207/10081; G06T 2207/30004; A61B 34/20;
(Continued)

(56) References Cited

U.S. PATENT DOCUMENTS

| | | | |
|---|---|---|---|
| 10,013,777 B2 * | 7/2018 | Mariampillai | A61B 6/505 |
| 2002/0090058 A1 * | 7/2002 | Yasuda | A61B 6/4464 378/205 |

(Continued)

FOREIGN PATENT DOCUMENTS

| | | |
|---|---|---|
| CN | 107789001 A | 3/2018 |
| WO | 2018234237 A1 | 12/2018 |

OTHER PUBLICATIONS

International Search Report in PCT/CN2019/085021 mailed on Jan. 23, 2020, 5 pages.
(Continued)

*Primary Examiner* — Siamak Harandi
*Assistant Examiner* — Daniella M. DiGuglielmo
(74) *Attorney, Agent, or Firm* — METIS IP LLC

(57) ABSTRACT

A method for positioning an object positioned on a table is provided. The method may include: obtaining a plan image, the plan image illustrating a virtual surface of the object; obtaining, by one or more capture devices, a 3-dimensional (3D) image, the 3D image including a set of elements corresponding to the object; obtaining a registration result by registering the plan image and the 3D image; determining whether the object needs to be moved based on the registration result; and in response to a determination that the object needs to be moved, causing the object to move according to the registration result.

20 Claims, 11 Drawing Sheets

(51) Int. Cl.
  *A61B 6/03*    (2006.01)
  *A61B 6/04*    (2006.01)
  *A61B 34/20*   (2016.01)
  *A61B 90/00*   (2016.01)
  *G06T 7/73*    (2017.01)
  *G16H 30/20*   (2018.01)
  *G16H 30/40*   (2018.01)
  *H04N 13/239*  (2018.01)
  *H04N 23/54*   (2023.01)
  *A61N 5/10*    (2006.01)

(52) U.S. Cl.
  CPC .............. *A61B 34/20* (2016.02); *A61B 90/37* (2016.02); *G06T 7/74* (2017.01); *G16H 30/20* (2018.01); *G16H 30/40* (2018.01); *A61B 6/0487* (2020.08); *A61B 2034/2057* (2016.02); *A61B 2090/365* (2016.02); *A61B 2090/372* (2016.02); *A61B 2090/3762* (2016.02); *A61N 2005/1059* (2013.01); *G06T 2207/10081* (2013.01); *G06T 2207/30004* (2013.01); *H04N 13/239* (2018.05); *H04N 23/54* (2023.01)

(58) Field of Classification Search
  CPC .................. A61B 90/37; A61B 6/0407; A61B 2034/2057; A61B 2090/365; A61B 2090/372; A61B 2090/3762; A61B 6/488; A61B 6/032; A61B 6/0487; A61B 6/5235; A61B 6/5247; A61B 5/055; G16H 30/20; G16H 30/40; H04N 13/329; H04N 23/54; H04N 13/239; A61N 5/1049; A61N 2005/1059; A61N 5/1069
  See application file for complete search history.

(56) References Cited

U.S. PATENT DOCUMENTS

| | | | |
|---|---|---|---|
| 2011/0002444 A1* | 1/2011 | Schmitt | A61B 6/469 378/205 |
| 2016/0174930 A1 | 6/2016 | Braun et al. | |
| 2017/0035374 A1* | 2/2017 | Schäfer | A61B 6/4441 |
| 2018/0116613 A1* | 5/2018 | Von Berg | A61B 8/40 |
| 2018/0315248 A1* | 11/2018 | Bastov | G06T 19/006 |
| 2019/0046134 A1* | 2/2019 | Imamura | A61B 6/464 |
| 2020/0330166 A1* | 10/2020 | Meglan | A61B 34/25 |

OTHER PUBLICATIONS

Written Opinion in PCT/CN2019/085021 mailed on Jan. 23, 2020, 5 pages.

* cited by examiner

SYSTEMS AND METHODS FOR OBJECT POSITIONING AND IMAGE-GUIDED SURGERY

CROSS-REFERENCE TO RELATED APPLICATIONS

This present application is a continuation of International Application No. PCT/CN2019/085021, filed on Apr. 29, 2019, the contents of which are hereby incorporated by reference.

TECHNICAL FIELD

The present disclosure generally relates to radiation therapy and image-guided surgery, and more particularly to systems and methods for augmented reality assisted object positioning and/or image-guided surgery.

BACKGROUND

In medical imaging (e.g., computed tomography (CT) imaging, magnetic resonance imaging (MRI), positron emission tomography-computed tomography (PET-CT) imaging, positron emission tomography-magnetic resonance imaging (PET-MRI), or the like) or radiation therapy (RT), a target of an object needs to be positioned so that the target can be located at an imaging isocenter of an imaging device or a treatment isocenter of a radiotherapy device. The positioning process is generally conducted before the imaging process or the RT process. The positioning process is generally complicated, time consuming, and/or has low accuracy, which may influence the efficiency of the imaging process or the RT process. Thus, it is desirable to provide systems and methods for positioning an object before an imaging process or radiotherapy process.

In a medical procedure (e.g., a surgery (e.g., CT-guided intervention)), an operator (e.g., an operating surgeon) is generally required to look back and forth between an object (e.g., a patient) and one or more monitors displaying patient anatomical information for guidance in operation. In this manner, a type of mental mapping is made by the operator to understand the location of a target structure. However, mental mapping is generally difficult and inaccurate. Therefore, it is desirable to provide systems and methods for facilitating image-guided surgery.

SUMMARY

In one aspect of the present disclosure, a method for positioning an object positioned on a table is provided. The method may include: obtaining a plan image, the plan image illustrating a virtual surface of the object; obtaining, by one or more capture devices, a 3-dimensional (3D) image, the 3D image including a set of elements corresponding to the object; obtaining a registration result by registering the plan image and the 3D image; determining whether the object needs to be moved based on the registration result; and/or in response to a determination that the object needs to be moved, causing the object to move according to the registration result.

In another aspect of the present disclosure, a method for positioning an object positioned on a table is provided. The method may include: obtaining a plan image, the plan image including a contour profile of the table determined in a treatment plan; determining a target position of the table based on the contour profile of the table; obtaining, by one or more capture devices, a 3-dimensional (3D) image, the 3D image including a first set of elements corresponding to the object and a second set of elements corresponding to the table; determining a current position of the table based on the 3D image; and/or causing the table to move based on the current position of the table and the target position of the table.

In another aspect of the present disclosure, a method for positioning an object positioned on a table is provided. The method may include: obtaining a plan image, the plan image including a virtual surface of the object; obtaining, by one or more capture devices, a 3-dimensional (3D) image, the 3D image including a set of elements corresponding to the object; obtaining a registration result by registering the 3D image with the plan image; determining whether the table needs to be moved based on the registration result; and/or in response to a determination that the table needs to be moved, causing the table to move according to the registration result.

In another aspect of the present disclosure, a method for guiding an operation of a medical instrument during a medical procedure is provided. The method may include: obtaining at least one medical image of an object; determining one or more regions of interest in each of the at least one medical image; generating, by one or more capture devices, a 3-dimensional (3D) image, the 3D image including a set of elements corresponding to the object; generating an augmented reality image by projecting at least one of the one or more regions of interest in the at least one medical image onto the 3D image; and/or providing the augmented reality image for guiding an operation of the medical instrument.

In another aspect of the present disclosure, a system for positioning an object positioned on a table is provided. The system may include: at least one storage device including a set of instructions or programs; and at least one processor configured to communicate with the at least one storage device. When executing the set of instructions or programs, the at least one processor may be configured to cause the system to perform operations including: obtaining a plan image, the plan image illustrating a virtual surface of the object; obtaining, by one or more capture devices, a 3-dimensional (3D) image, the 3D image including a set of elements corresponding to the object; obtaining a registration result by registering the plan image and the 3D image; determining whether the object needs to be moved based on the registration result; and/or in response to a determination that the object needs to be moved, causing the object to move according to the registration result.

In another aspect of the present disclosure, a system for positioning an object positioned on a table is provided. The system may include: at least one storage device including a set of instructions or programs; and at least one processor configured to communicate with the at least one storage device. When executing the set of instructions or programs, the at least one processor may be configured to cause the system to perform operations including: obtaining a plan image, the plan image including a contour profile of the table determined in a treatment plan; determining a target position of the table based on the contour profile of the table; obtaining, by one or more capture devices, a 3-dimensional (3D) image, the 3D image including a first set of elements corresponding to the object and a second set of elements corresponding to the table; determining a current position of the table based on the 3D image; and/or causing the table to move based on the current position of the table and the target position of the table.

In another aspect of the present disclosure, a system for positioning an object positioned on a table is provided. The system may include: at least one storage device including a set of instructions or programs; and at least one processor configured to communicate with the at least one storage device. When executing the set of instructions or programs, the at least one processor may be configured to cause the system to perform operations including: obtaining a plan image, the plan image including a virtual surface of the object; obtaining, by one or more capture devices, a 3-dimensional (3D) image, the 3D image including a set of elements corresponding to the object; obtaining a registration result by registering the 3D image with the plan image; determining whether the table needs to be moved based on the registration result; and/or in response to a determination that the table needs to be moved, causing the table to move according to the registration result.

In another aspect of the present disclosure, a system for guiding an operation of a medical instrument during a medical procedure is provided. The system may include: at least one storage device including a set of instructions or programs; and at least one processor configured to communicate with the at least one storage device. When executing the set of instructions or programs, the at least one processor may be configured to cause the system to perform operations including: obtaining at least one medical image of an object; determining one or more regions of interest in each of the at least one medical image; generating, by one or more capture devices, a 3-dimensional (3D) image, the 3D image including a set of elements corresponding to the object; generating an augmented reality image by projecting at least one of the one or more regions of interest in the at least one medical image onto the 3D image; and/or providing the augmented reality image for guiding an operation of the medical instrument.

In another aspect of the present disclosure, a system for positioning an object positioned on a table is provided. The system may include: an acquisition unit configured to obtain a plan image, the plan image illustrating a virtual surface of the object, and obtain, from one or more capture devices, a 3-dimensional (3D) image, the 3D image including a set of elements corresponding to the object; a registration unit configured to obtain a registration result by registering the plan image and the 3D image; and a control unit configured to determine whether the object needs to be moved based on the registration result, and in response to a determination that the object needs to be moved, cause the object to move according to the registration result.

In another aspect of the present disclosure, a system for positioning an object positioned on a table is provided. The system may include: an acquisition unit configured to obtain a plan image, the plan image including a contour profile of the table determined in a treatment plan, and obtain, from one or more capture devices, a 3-dimensional (3D) image, the 3D image including a first set of elements corresponding to the object and a second set of elements corresponding to the table; and a control unit configured to determine a target position of the table based on the contour profile of the table, determine a current position of the table based on the 3D image, and cause the table to move based on the current position of the table and the target position of the table.

In another aspect of the present disclosure, a system for positioning an object positioned on a table is provided. The system may include: an acquisition unit configured to obtain a plan image, the plan image including a virtual surface of the object, and obtain, from one or more capture devices, a 3-dimensional (3D) image, the 3D image including a set of elements corresponding to the object; a registration unit configured to obtain a registration result by registering the 3D image with the plan image; and a control unit configured to determine whether the table needs to be moved based on the registration result, and in response to a determination that the table needs to be moved, cause the table to move according to the registration result.

In another aspect of the present disclosure, a system for guiding an operation of a medical instrument during a medical procedure is provided. The system may include: an acquisition unit configured to obtain at least one medical image of an object; a control unit configured to determine one or more regions of interest in each of the at least one medical image; a reconstruction unit configured to generate, from one or more capture devices, a 3-dimensional (3D) image, the 3D image including a set of elements corresponding to the object; a projection unit configured to generate an augmented reality image by projecting at least one of the one or more regions of interest in the at least one medical image onto the 3D image; and a display unit configured to provide the augmented reality image for guiding an operation of the medical instrument.

In another aspect of the present disclosure, a non-transitory computer readable medium is provided. The non-transitory computer readable medium may store instructions. The instructions, when executed by at least one processor, may cause the at least one processor to implement a method comprising: obtaining a plan image, the plan image illustrating a virtual surface of the object; obtaining, by one or more capture devices, a 3-dimensional (3D) image, the 3D image including a set of elements corresponding to the object; obtaining a registration result by registering the plan image and the 3D image; determining whether the object needs to be moved based on the registration result; and/or in response to a determination that the object needs to be moved, causing the object to move according to the registration result.

In another aspect of the present disclosure, a non-transitory computer readable medium is provided. The non-transitory computer readable medium may store instructions. The instructions, when executed by at least one processor, may cause the at least one processor to implement a method comprising: obtaining a plan image, the plan image including a contour profile of the table determined in a treatment plan; determining a target position of the table based on the contour profile of the table; obtaining, by one or more capture devices, a 3-dimensional (3D) image, the 3D image including a first set of elements corresponding to the object and a second set of elements corresponding to the table; determining a current position of the table based on the 3D image; and/or causing the table to move based on the current position of the table and the target position of the table.

In another aspect of the present disclosure, a non-transitory computer readable medium is provided. The non-transitory computer readable medium may store instructions. The instructions, when executed by at least one processor, may cause the at least one processor to implement a method comprising: obtaining a plan image, the plan image including a virtual surface of the object; obtaining, by one or more capture devices, a 3-dimensional (3D) image, the 3D image including a set of elements corresponding to the object; obtaining a registration result by registering the 3D image with the plan image; determining whether the table needs to be moved based on the registration result; and/or in response to a determination that the table needs to be moved, causing the table to move according to the registration result.

In another aspect of the present disclosure, a non-transitory computer readable medium is provided. The non-transitory computer readable medium may store instructions. The instructions, when executed by at least one processor, may cause the at least one processor to implement a method comprising: obtaining at least one medical image of an object; determining one or more regions of interest in each of the at least one medical image; generating, by one or more capture devices, a 3-dimensional (3D) image, the 3D image including a set of elements corresponding to the object; generating an augmented reality image by projecting at least one of the one or more regions of interest in the at least one medical image onto the 3D image; and/or providing the augmented reality image for guiding an operation of the medical instrument.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
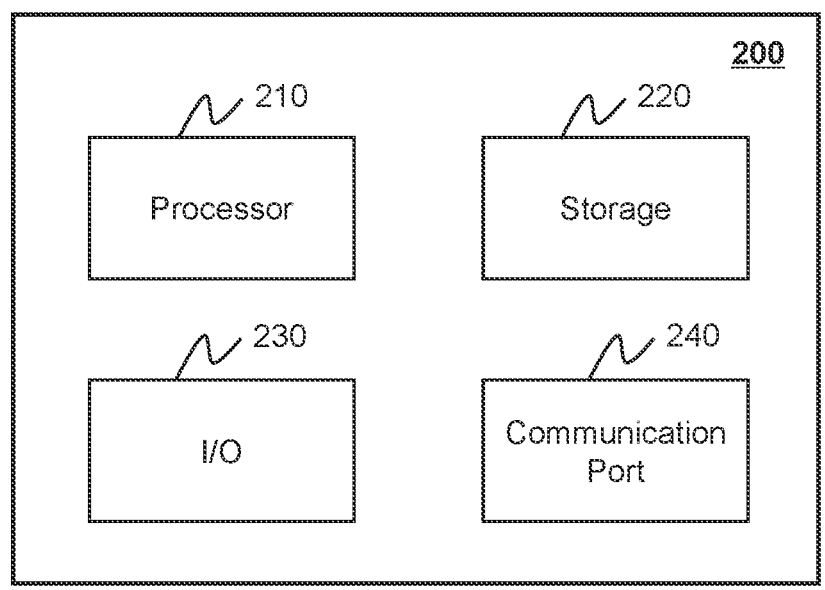
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems with one or more augmented reality (AR) visualization components for medical or industrial application, such as for disease treatment, disease diagnosis, synchronous motion control, research purposes, etc. In some embodiments, the system may be a radiation therapy (RT) system, a computed tomography (CT) system, an ultrasonography system, an X-ray photography system, a magnetic resonance imaging (MRI) system, a positron emission tomography-computed tomography (PET-CT) imaging system, a positron emission tomography-magnetic resonance imaging (PET-MRI) system, or the like, or any combination thereof. The following descriptions are provided with reference to an RT system (or CT system) for illustration purposes and not intended to limit the scope of the present disclosure. In one aspect of the present disclosure, the AR visualization technology is used for positioning an object positioned on a table. With the assistance of AR visualization, the positioning process can be simplified and/or automated, and accordingly the efficiency and/or the accuracy of the positioning process can be improved. In another aspect of the present disclosure, the AR technology is also used for guiding an operation of a medical instrument during a medical procedure. With the assistance of AR visualization, the operation of the medical instrument may be simplified, automated and/or semi-automated, and accordingly the efficiency and/or the accuracy of the operation process can be improved, which can reduce trauma to the object from the operation and/or the imaging process accompanying the operation.

Figure 1:
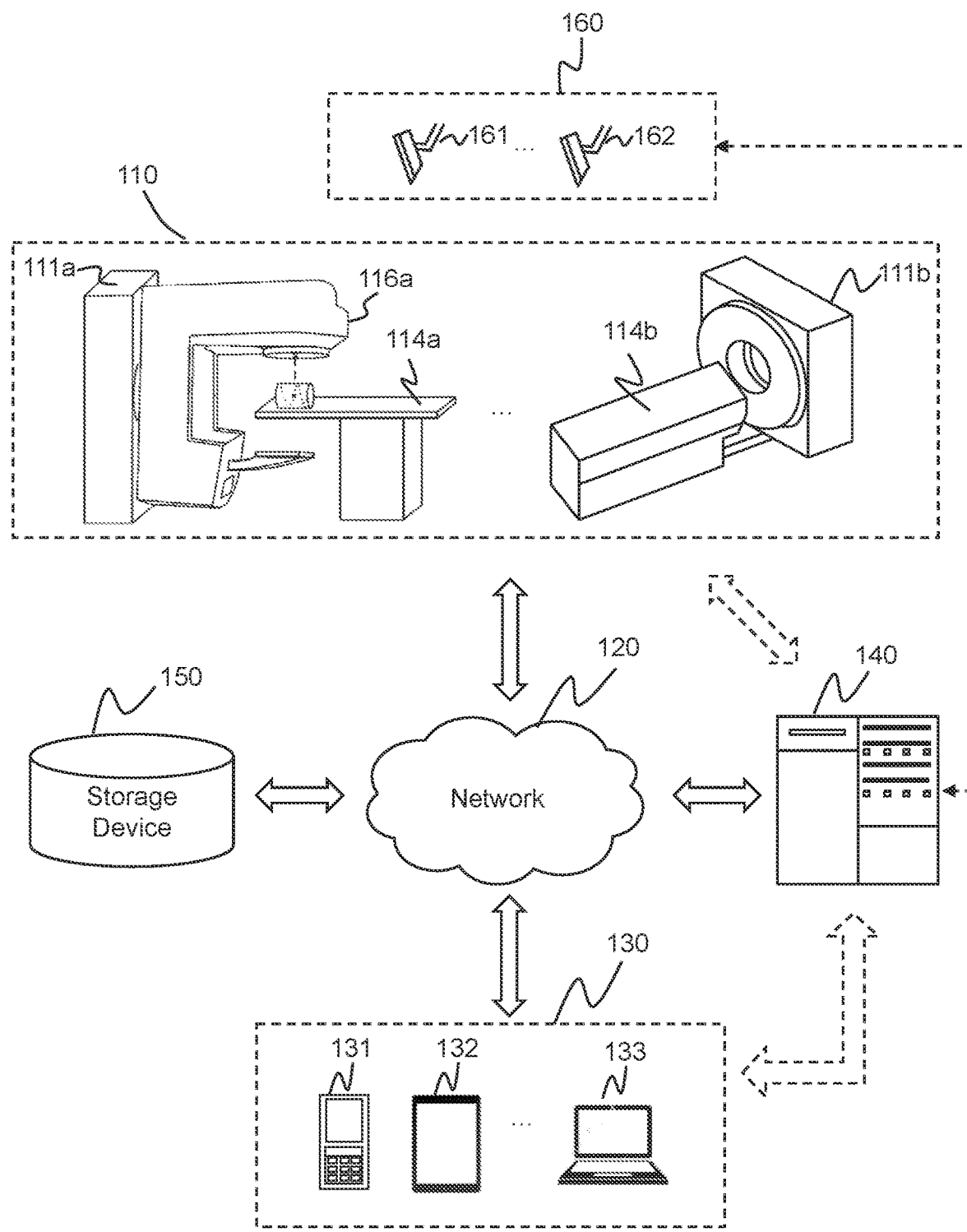
FIG. 1 is a schematic diagram illustrating an exemplary system according to some embodiments of the present disclosure.

FIG. 1 is a schematic diagram illustrating an exemplary system according to some embodiments of the present disclosure. As shown in FIG. 1, the system 100 may include an apparatus 110, a network 120, one or more terminals 130, a processing device 140, and a storage device 150. In some embodiments, the system 100 may include one or more capture devices 160. The components in the system 100 may be connected in one or more of various ways. Merely by way of example, the apparatus 110 may be connected to the processing device 140 through the network 120. As another example, the apparatus 110 may be connected to the processing device 140 directly as indicated by the bi-directional arrow in dotted lines linking the apparatus 110 and the processing device 140. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120. As still another example, the capture device 160 may be connected to the processing device 140 directly or through the network 120.

In some embodiments, the apparatus 110 may be an RT device. In some embodiments, the RT device may deliver a radiation beam to an object (e.g., a patient, or a phantom) or a portion thereof. In some embodiments, the RT device may include a linear accelerator (also referred to as "linac"). The linac may generate and emit a radiation beam (e.g., an X-ray beam) from a treatment head 116a. The radiation beam may pass through one or more collimators (e.g., a multi-leaf collimator (MLC)) of certain shapes, and enter into the object. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head 116a may be coupled to a gantry 111a. The gantry 111a may rotate, for example, clockwise or counter-clockwise around a gantry rotation axis. In some embodiments, the treatment head 116a may rotate along with the gantry 116. In some embodiments, the RT device may include a table 114a configured to support the object during radiation treatment.

In some embodiments, the apparatus 110 may be an imaging device. The imaging device may generate or provide image(s) via scanning an object or a part of the object. In some embodiments, the imaging device may be a medical imaging device, for example, a positron emission tomography (PET) device, a single-photon emission computed tomography (SPECT) device, a computed tomography (CT) device, a magnetic resonance imaging (MRI) device, an ultrasonography device, an X-ray photography device, or the like, or any combination thereof. In some embodiments, the imaging device may include a gantry 111b to support one or more imaging components configured to imaging the object, and/or a table 114b configured to support the object during an imaging process. In some embodiments, the imaging device may include a single-modality scanner. The single-modality scanner may include an MRI scanner, a CT scanner, a PET scanner, or the like, or any combination thereof. In some embodiments, the imaging device may include a multi-modality scanner. The multi-modality scanner may include a positron emission tomography-computed tomography (PET-CT) scanner, a positron emission tomography-magnetic resonance imaging (PET-MRI) scanner, or the like, or any combination thereof. In some embodiments, the imaging device may transmit the image(s) via the network 120 to the processing device 140, the storage device 150, and/or the terminal(s) 130. For example, the image(s) may be sent to the processing device 140 for further processing or may be stored in the storage device 150.

In some embodiments, the apparatus 110 may be an integrated device of an imaging device and an RT device. In some embodiments, the apparatus 110 may include one or more surgical instruments. In some embodiments, the apparatus 110 may include an operating table (or table for brevity) configured to support an object during surgery. The table 114a or 114b may support an object during a treatment process or imaging process, and/or support a phantom during a correction process of the apparatus 110. The table 114a or 114b may be adjustable and/or movable to suit for different application scenarios.

In some embodiments, the object to be treated or scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc. In the present disclosure, "object" and "subject" are used interchangeably.

The network 120 may include any suitable network that can facilitate exchange of information and/or data for the system 100. In some embodiments, one or more components of the system 100 (e.g., the apparatus 110, the terminal 130, the processing device 140, the storage device 150, etc.) may communicate information and/or data with one or more other components of the system 100 via the network 120. For example, the processing device 140 may obtain one or more instructions from the terminal 130 via the network 120. As another example, the processing device 140 may obtain one or more images from the apparatus 110 or the storage device 150 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the system 100 may be connected to the network 120 to exchange data and/or information.

Figure 3:
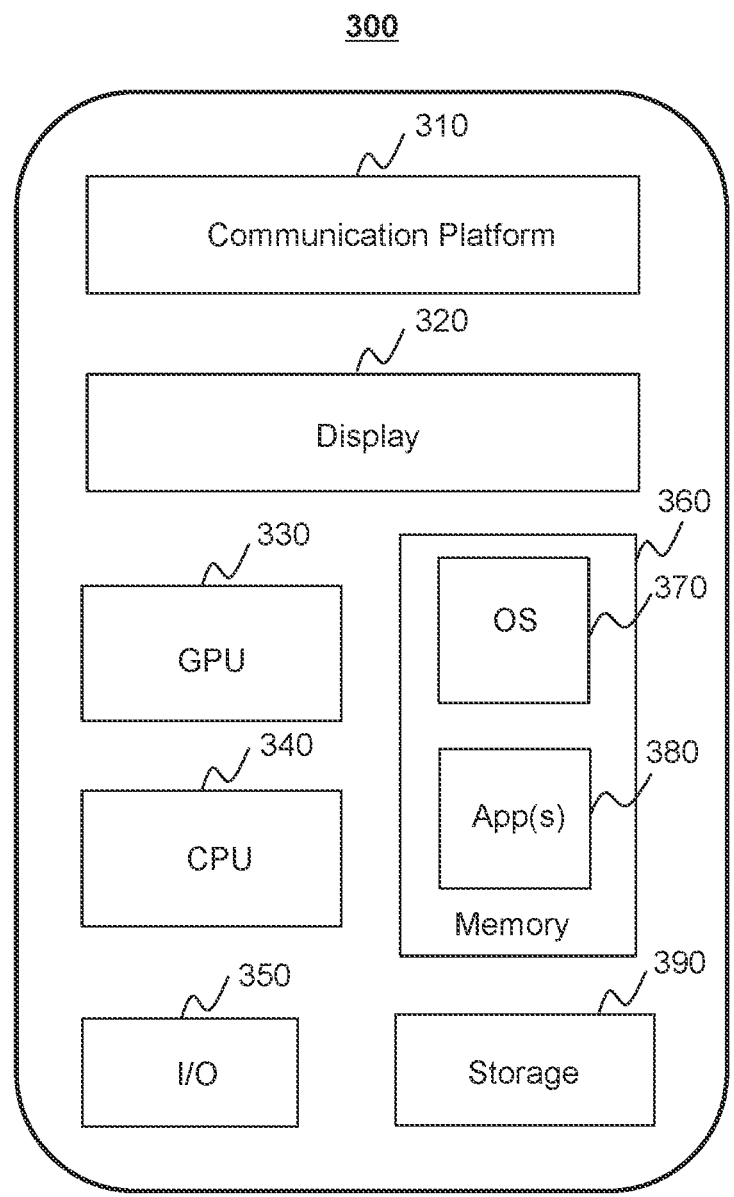
FIG. 3 is a schematic diagram illustrating exemplary hardware and/or software components of an exemplary mobile device according to some embodiments of the present disclosure.

The terminal(s) 130 may enable interactions between a user and the system 100. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VRM™, etc. In some embodiments, the terminal(s) 130 may be part of the processing device 140.

The processing device 140 may process data and/or information obtained from the apparatus 110, the terminal 130, and/or the storage device 150. For example, the processing device 140 may obtain a plan image. As another example, the processing device 140 may obtain a 3D image. As still another example, the processing device 140 may obtain a registration result by registering the plan image and the 3D image. As still another example, the processing device 140 may determine whether the table and/or the object needs to be moved based on the registration result. As a further example, the processing device 140 may cause the table and/or object to move according to the registration result. As a further example, the processing device 140 may determine a target position of the table based on a contour profile of the table, determine a current position of the table based on the 3D image, and/or cause the table to move based on the current position of the table and the target position of the table.

As still a further example, the processing device 140 may obtain at least one medical image of an object. As still a further example, the processing device 140 may determine one or more regions of interest in each of the at least one medical image. As still a further example, the processing device 140 may generate a 3D image. As still a further example, the processing device 140 may generate an augmented reality image by projecting at least one of the one or more regions of interest in the at least one medical image onto the 3D image. As still a further example, the processing device 140 may provide the augmented reality image for guiding an operation of a medical instrument.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the apparatus 110, the terminal 130, and/or the storage device 150 via the network 120. As another example, the processing device 140 may be directly connected to the apparatus 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the apparatus 110, the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the system 100 (e.g., the processing device 140, the terminal 130, etc.). One or more components in the system 100 may access the data or instructions stored in the storage device 150 via the network 120. In some embodiments, the storage device 150 may be directly connected to or communicate with one or more other components in the system 100 (e.g., the processing device 140, the terminal 130, etc.). In some embodiments, the storage device 150 may be part of the processing device 140. In some embodiments, the processing device 140 may be connected to or communicate with the apparatus 110 via the network 120, or at the backend of the processing device 140.

In some embodiments, the capture device(s) 160 may be configured to capture one or more images (or videos) of the object and/or the table. In some embodiments, the capture device(s) 160 may include one or more digital cameras. In some embodiments, the capture device(s) 160 may include one or more depth cameras. In some embodiments, the capture device(s) 160 may include one or more monocular cameras, one or more binocular cameras, or the like, or a combination thereof. In some embodiments, the image(s) captured by the capture device(s) 160 may be two-dimensional (2D) image(s), three-dimensional (3D) image(s), or the like, or a combination thereof. In some embodiments, the image(s) captured by the capture device(s) 160 may be real scene image(s) of the object and/or the table. In some embodiments, the image(s) captured by the capture device 160 may include depth information of the object and/or the table. In some embodiments, the capture device(s) 160 may be mounted (or installed) at fixed position(s) relative to the apparatus 110 (e.g., mounted on the ceiling of an operating room that accommodates the apparatus 110). In some embodiments, the capture device(s) 160 may be positioned such that the capture device(s) 160 can capture relatively clear image(s) of the object and/or the table within a relatively wide field of vision. In some embodiments, the capture devices 160 may be mounted at different positions such that the capture devices 160 may capture images of the object and/or the table from different directions (or angles). In some embodiments, the fields of view of the capture devices 160 may at least partially overlap and the capture devices 160 may capture images including at least one same region of the object and/or the table from different directions (or angles). For example, a first capture device 161 and a second capture device 162 may capture images of the object and/or the table from 45 degrees on the upper left and 45 degrees on the upper right of the object and/or the table, respectively.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process image(s) obtained from the apparatus 110, the terminal 130, the storage device 150, the capture device 160, and/or any other component of the system 100. In some embodiments, the processor 210 may process the image(s) based on information relating to a treatment plan. The treatment plan may be obtained from a treatment planning system (TPS) associated with the system 100. The information relating to the treatment plan may include preoperative medical image(s) representing the internal anatomical information of an object to be treated or imaged. In some embodiments, the processor 210 may generate augmented reality (AR) image(s) based on the image(s) or information obtained from the terminal 130, the storage device 150, the capture device 160, and/or any other component of the system 100. The AR image(s) may represent the external surface information of the object and/or the internal anatomical information of the object. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the apparatus 110, the terminal 130, the storage device 150, and/or any other component of the system 100. In some embodiments, the storage 220 may include amass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for positioning an object (or a table) and/or a program for guiding an operation of a medical instrument (e.g., a biopsy needle).

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the apparatus 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
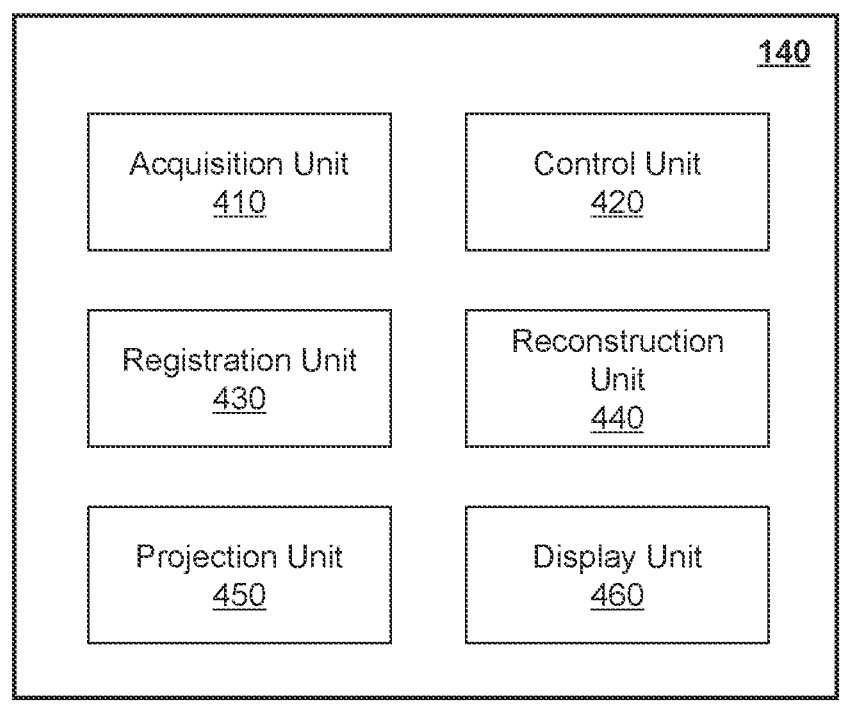
FIG. 4 is a block diagram illustrating an exemplary processing device according to some embodiments of the present disclosure.

FIG. 4 is a block diagram illustrating an exemplary processing device according to some embodiments of the present disclosure. The processing device 140 may include an acquisition unit 410, a control unit 420, a registration unit 430, a reconstruction unit 440, a projection unit 450, and a display unit 460.

The acquisition unit 410 may acquire data. The acquisition unit 410 may acquire data from one or more of the apparatus 110, the network 120, the terminal 130, the storage device 150, the capture device 160 or any devices or components disclosed in the present disclosure capable of storing data. The acquired data may include image data of the object, user instructions, algorithms, or the like, or a combination thereof. In some embodiments, image data of the object may include AR images, AR videos, preoperative medical image data etc. In some embodiments, the acquisition unit 410 may obtain position information of the table determined in a treatment plan. In some embodiments, the acquisition unit 410 may obtain a contour profile of the table determined in a treatment plan. In some embodiments, the acquisition unit 410 may obtain a plan image including the contour profile of the table determined in the treatment plan and/or a virtual surface of the object. In some embodiments, the acquisition unit 410 may acquire at least two images of the object and the table (e.g., from at least two capture devices). In some embodiments, the acquisition unit 410 may obtain one or more medical images (e.g., tomography images) of the object. In some embodiments, the acquisition unit 410 may obtain one or more medical images of an object generated during a first time period. In some embodiments, the medical images of the object may include computed tomography (CT) images, magnetic resonance (MR) images, ultrasound images, or the like, or any combination thereof. For example, the set of medical images may include four-dimensional (4D) CT images of the object. In some embodiments, the acquisition unit 410 may acquire one or more images of the object during a second time period (e.g., from one or more capture devices). In some embodiments, the acquisition unit 410 may obtain a first waveform of a motion generated during the first time period. In some embodiments, the acquisition unit 410 may acquire a second waveform of the motion generated during the second time period. More descriptions of the acquisition unit 410 may be found elsewhere in the present disclosure (e.g., FIGS. 5-11 and descriptions thereof).

The control unit 420 may control operations of modules or components of the system 100. In some embodiments, the control unit 420 may cause the table to move (e.g., to a target position) based on an augmented reality image. In some embodiments, the control unit 420 may cause the object to move to a target position based on an augmented reality image. In some embodiments, the control unit 420 may determine one or more regions of interest in one or more medical images. In some embodiments, the control unit 420 may determine a reference phase in a waveform. In some embodiments, the control unit 420 may determine a target position of the table. More descriptions of the control unit 420 may be found elsewhere in the present disclosure (e.g., FIGS. 5-11 and descriptions thereof).

The registration unit 430 may register at least two images. In some embodiments, the registration unit 430 may generate a 3D image by registering two images. In some embodiments, the registration unit 430 may obtain a registration result (see FIGS. 7-8) by registering a plan image and a 3D image. In some embodiments, the registration unit 430 may register the at least two images (or a portion thereof) using one or more image registration algorithms (e.g., a grayscale and template based registration algorithm, a feature based registration algorithm, a domain transformation based registration algorithm, etc.). In some embodiments, the registration unit 430 may register at least one region of interest and a dynamic image in time and space. In some embodiments, the region of interest may include a contour profile of the table and/or a contoured surface (or profile) of the object. In some embodiments, the region of interest may include a plurality of elements corresponding to a portion of the object (e.g., an organ like a lung, a liver, a heart, etc.). More descriptions of the registration unit 430 may be found elsewhere in the present disclosure (e.g., FIGS. 5-11 and descriptions thereof).

The reconstruction unit 440 may generate a 3D image based on one or more images. In some embodiments, the reconstruction unit 440 may generate a dynamic image (or video) by fusing at least two images (or dynamic images, or videos). In some embodiments, the reconstruction unit 440 may reconstruct a virtual surface of an object (or a plan image) based on one or more medical images. More descriptions of the reconstruction unit 440 may be found elsewhere in the present disclosure (e.g., FIGS. 5-11 and descriptions thereof).

The projection unit 450 may project virtual information onto a real image to generate an AR image. In some embodiments, the projection unit 450 may project a contour profile of the table onto a 3D image. In some embodiments, the projection unit 450 may project a virtual surface of the object onto a 3D image. In some embodiments, the projection unit 450 may project at least one region of interest in a set of medical images onto a dynamic image. In some embodiments, the projection unit 450 may project at least one region of interest in a medical image onto a frame of a dynamic image. More descriptions of the projection unit 450 may be found elsewhere in the present disclosure (e.g., FIGS. 5-11 and descriptions thereof).

The display unit 460 may display information. In some embodiments, the displayed information may guide an operation of an operator or a medical instrument. In some embodiments, the display unit 460 may display position information of the table. In some embodiments, the display unit 460 may display images (or videos) of the table and/or object. In some embodiments, the display unit 460 may display a virtual surface of the object, one or more regions of interest of the object, a contour profile of the table, etc. In some embodiments, the operator may adjust the position of the table according to the displayed information. More descriptions of the display unit 460 may be found elsewhere in the present disclosure (e.g., FIGS. 5-11 and descriptions thereof).

In some embodiments, one or more units illustrated in FIG. 4 may be implemented in at least part of the system 100 as illustrated in FIG. 1. For example, the acquisition unit 410, the control unit 420, the registration unit 430, the reconstruction unit 440, the projection unit 450 and/or the display unit 460 may be integrated into a console (not shown). Via the console, a user may set parameters for implementing operations (e.g., a treatment plan for treating an object) described elsewhere in the present disclosure. In some embodiments, the console may be implemented via the processing device 140 and/or the terminal 130.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the processing device 140 may further include an I/O unit for facilitating interactions between the system 100 and a user.

Figure 5:
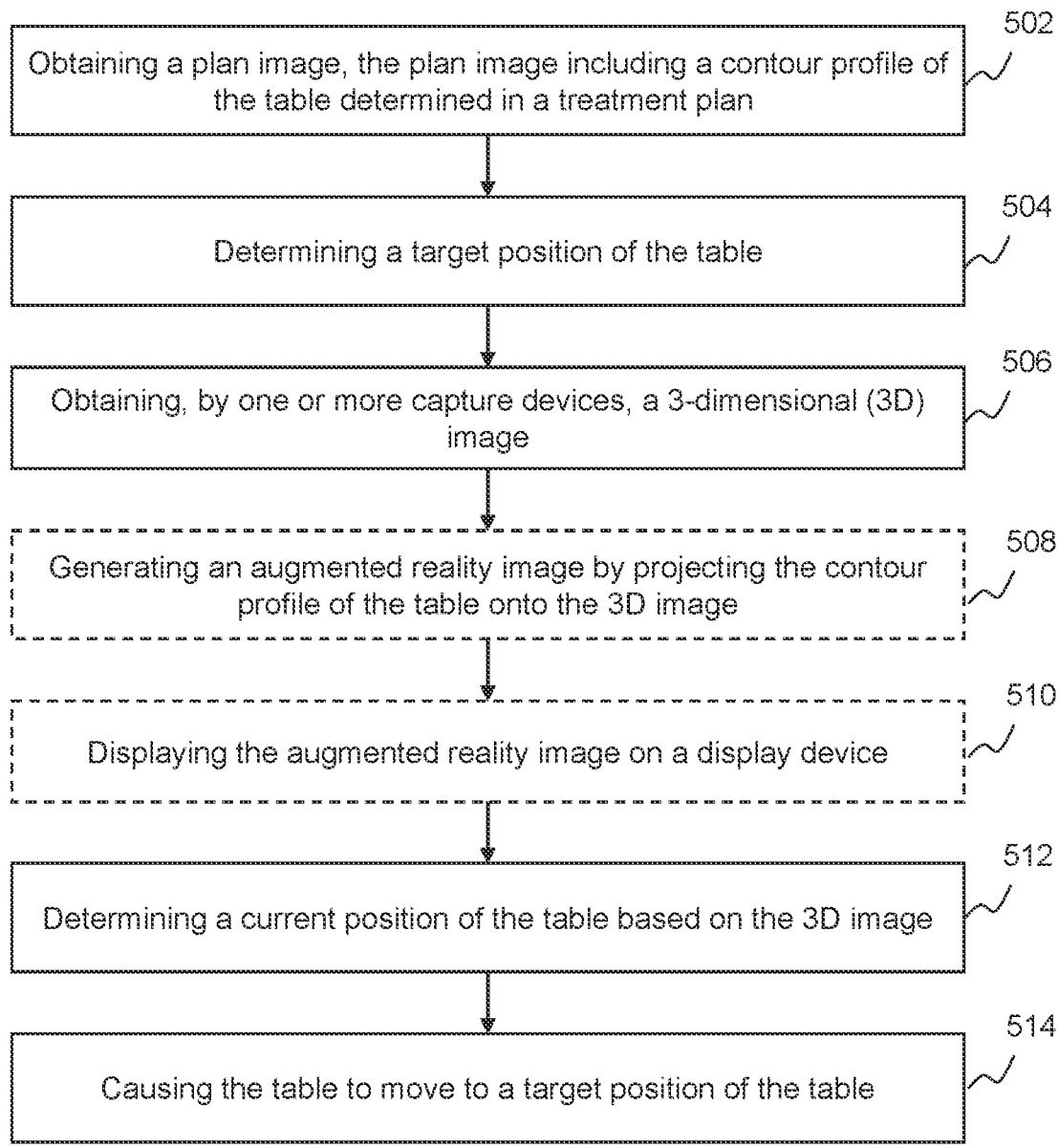
FIG. 5 is a flowchart illustrating an exemplary process for positioning a table according to some embodiments of the present disclosure.

FIG. 5 is a flowchart illustrating an exemplary process for positioning a table according to some embodiments of the present disclosure. In some embodiments, at least part of process 500 may be performed by the processing device 140 (implemented in, for example, the computing device 200 shown in FIG. 2). For example, the process 500 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In some embodiments, the process 500 may be performed before an imaging process or a treatment process to position an object supported by a table of the apparatus 110, such that a target portion of the object may be located at (or in the vicinity of) an imaging isocenter of an imaging device or a treatment isocenter of a radiotherapy device. After the object is positioned, the imaging process or the treatment process may be started. For example, after the object is positioned, the object may be treated by radiation rays generated by an RT device. As another example, after the object is positioned, the object may be scanned by a CT imaging device to generate an image (e.g., a scout image) of the object. In some embodiments, because the object is supported on the table, the table may be positioned first, and then the position of the object may be adjusted relative to the table. In some embodiments, the position of the object relative to the table may be adjusted first, and then the table may be positioned. A positioning process for radiation treatment illustrated below is merely provided for the purposes of illustration, and not intended to limit the scope of the present disclosure. A positioning process for imaging may be made under the teachings of the present disclosure.

In 502, a plan image may be obtained. The plan image may include a contour profile of the table determined in a treatment plan. The plan image including the contour profile of the table may be obtained by the processing device (e.g., the acquisition unit 410). In some embodiments, the contour profile of the table determined in the treatment plan may be a virtual contour profile. Before an RT process, a treatment plan may need to be generated in a treatment planning system (TPS). During the treatment planning procedure, the virtual contour profile of the table, the position information of the object relative to the table may be specified.

In 504, a target position of the table may be determined. In some embodiments, the target position of the table may be determined by the processing device (e.g., the control unit 420). The target position of the table may be determined based on the contour profile of the table. In some embodiments, the target position of the table, a target position of the object relative to the table, and/or a posture of the object may be specified in the treatment plan. In some embodiments, before the treatment plan is generated in the TPS, a target position of the table, a target position of the object relative to the table, and/or a posture of the object may be specified.

In 506, a 3-dimensional (3D) image may be obtained. In some embodiments, the 3D image may be generated based on at least two images. In some embodiments, the at least two images may be acquired by the processing device (e.g., the acquisition unit 410). In some embodiments, the at least two images may be captured (or generated) by at least two capture devices (e.g., the first capture device 161 and the second capture device 162). In some embodiments, each capture device of the at least two capture devices may capture one of the at least two images. The at least two images may include at least one same region of the object and/or the table from different directions (or angles). In some embodiments, the at least two images may be real scene images of the object and/or the table in different view angles. For example, the first capture device 161 and the second capture device 162 may capture the images of the object and/or the table from different view angles (e.g., 45 degrees on the upper left and 45 degrees on the upper right, respectively). In some embodiments, the at least two images may include depth information of the object and/or the table. In some embodiments, the at least two capture devices may automatically capture the images of the object and/or the table during the positioning process consistently or periodically, and the images may be transmitted to the processing device 140 and/or the storage device 150 in real time, such that the processing device 140 may obtain the images. In some embodiments, the processing device 140 may transmit instruction(s) for capturing images of the object and/or the table to the capture devices, such that the capture devices may capture the images and transmit the images to the processing device 140.

In some embodiments, the 3D image may be generated based on the at least two images. In some embodiments, the 3D image may be generated by the processing device 140 (e.g., the reconstruction unit 440). In some embodiments, the processing device 140 may reconstruct the 3D image based on one or more image reconstruction algorithms (e.g., monocular vision algorithm, stereo vision algorithm, shape from shading algorithm, etc.). In some embodiments, the processing device 140 (e.g., the registration unit 430) may register the at least two images before reconstructing the 3D image based on the at least two images. In some embodiments, the processing device 140 (e.g., the registration unit 430) may register the at least two images (or a portion thereof) using one or more image registration algorithms (e.g., grayscale and template based registration algorithm, feature based registration algorithm, domain transformation based registration algorithm, etc.). In some embodiments, the processing device 140 may pre-process the at least two images before registering the at least two images. Exemplary pre-processing may include denoising, image enhancing, image segmentation, etc.

In some embodiments, the 3D image may include a first set of elements (e.g., pixels) corresponding to the object and a second set of elements (e.g., pixels) corresponding to the table. In some embodiments, the first set of elements corresponding to the object may represent the object in the 3D image. The second set of elements corresponding to the table may represent the table in the 3D image. In some embodiments, the object may be a patient supported on the table. In some embodiments, the processing device 140 may segment the 3D image and obtain the first set of elements and the second set of elements. In some embodiments, the processing device 140 may render the first set of elements and/or the second set of elements so that the first set of elements and the second set of elements are easy to distinguish visually. For example, the first set of elements and the second set of elements may have contour lines shown in different colors which may represent the real contour profiles of the patient and the table, respectively. As another example, the first set of elements and the second set of elements may be represented by blocks of different colors, in which the boundaries of the blocks may represent the real contour profiles of the patient and the table, respectively.

In 508, an AR image may be generated by projecting the contour profile of the table obtained in 502 onto the 3D image. The AR image may be generated by the processing device 140 (e.g., the projection unit 450). In some embodiments, the processing device 140 may fuse the contour profile of the table and the 3D image to generate the AR image. In some embodiments, the 3D image and the plan image including the contour profile of the table may be presented in the same coordinate system. The processing device 140 may directly superimpose the contour profile of the table on the 3D image. In some embodiments, the 3D image and the plan image including the contour profile of the table may be presented in different coordinate systems. The processing device 140 may convert the plan image including the contour profile of the table from its original coordinate system into the coordinate system of the 3D image, and then superimpose the contour profile of the table on the 3D image. In some embodiments, the 3D image may include the second set of elements corresponding to the table. The second set of elements may represent the real contour profile of the table. The contour profile of the table obtained in operation 502 may be a virtual contour profile of the table. Therefore, the AR image generated by projecting the virtual contour profile of the table onto the 3D image may include the second set of elements representing the real contour profile of the table and the virtual contour profile of the table.

In 510, the AR image may be displayed on a display device. The AR image may be displayed by the processing device 140 (e.g., the display unit 460). In some embodiments, the display unit 460 may include a video display (e.g., an electroluminescent display, an electronic paper, a light-emitting diode (LED) display, a liquid crystal display (LCD), a plasma display, a digital micromirror device (DMD), a liquid on silicon display, a field emission display, a laser color video display, a quantum dot display, an interferometric modulator display, a flexible display, etc.), a non-video display (e.g., a vacuum fluorescent display, a seven segment display, etc.), a 3D display (e.g., a holographic display, a retina display, a fog display, etc.), or the like, or a combination thereof. An exemplary display may be a head mounted display (HMD), a display device (e.g., a flat panel display or a curved panel display), or the like. In some embodiments, an operator can observe the AR image from the display device. In some embodiments, the AR image may be directly displayed on the table and/or the RT apparatus to guide an operation, e.g., positioning of the object by, e.g., the object himself or with the assistance of the operator.

In 512, a current position of the table may be determined based on the 3D image. The current position of the table may be determined by the processing device 140 (e.g., the control unit 420). In some embodiments, as described in connection with 506, the 3D image may include the second set of elements corresponding to the object. The second set of elements corresponding to the table may represent real contour profile of the table in the 3D image. The current position of the table may be determined based on the real contour profile of the table in the 3D image.

In 514, the table may be caused to move based on the current position of the table and the target position of the table. The table may be caused to move by the processing device 140 (e.g., the control unit 420). In some embodiments, the target position of the table may be predetermined in the treatment plan, for example, during treatment planning, the virtual contour profile of the table may be positioned at the target position. In some embodiments, because the target positions of the table relative to the apparatus 110 are specified and identical during the treatment planning process and the positioning process, the virtual contour profile of the table and the real contour profile of the table may be represented in the same coordinate system. The target position of the table may correspond to a position that the real contour profile of the table is coincident with the virtual contour profile of the table. Therefore, if the real contour profile of the table is coincident with the virtual contour profile of the table, the table may have arrived at the target position.

In some embodiments, the virtual contour profile of the table and the real contour profile of the table may be represented in different coordinate systems. For example, the virtual contour profile of the table may be represented by a plurality of elements having coordinates in a digital imaging and communications in medicine (DICOM) coordinate system. The real contour profile of the table may be represented by a plurality of elements having coordinates in an international electrotechnical commission (IEC) coordinate system. The processing device 140 (e.g., the control unit 420) may transform coordinates of the plurality of elements representing the virtual contour profile of the table from the DICOM coordinate system into the IEC coordinate system based on a predetermined conversion relationship (e.g., a rotation matrix).

In some embodiments, after displaying the AR image on the display device, an operator may determine whether the real contour profile of the table is coincident with the virtual contour profile of the table. If the operator determines that the real contour profile of the table is not coincident with the virtual contour profile of the table, the operator may send one or more instructions to the processing device 140, the acquisition unit 410 of the processing device 140 may receive the instruction(s), and then the control unit 420 of the processing device 140 may cause the table to move according to the instruction(s). In some embodiments, the operator may press (or operate) one or more operating keys (or buttons, handles) associated with the movement of the table so that the instruction(s) may be sent to the processing device. In this way, the operator may determine to move the table continuously or intermittently. For example, the operator may press (or operate) the operating keys (or buttons, handles) continuously, the processing device 140 may cause the table to move continuously, and the operator may observe the real time change of the position of the real contour profile of the table from the AR image (or video) displayed in the display device, until the operator determines that the real contour profile of the table is coincident with the virtual contour profile of the table, the operator may stop pressing (or operating) the operating keys (or buttons, handles), the processing device 140 may cause the table to stop moving, and the table is positioned at the target position of the table. As another example, the operator may press (or operate) the operating keys (or buttons, handles) intermittently, the processing device 140 may cause the table to move intermittently, and the operator may timely observe the change of the position of the real contour profile of the table from the AR image (or video) displayed in the display device, until the operator determines that the real contour profile of the table is coincident with the virtual contour profile of the table, the operator may stop pressing (or operating) the operating keys (or buttons, handles), the processing device 140 may cause the table to stop moving, and the table is positioned at the target position of the table. In some embodiments, the table may be caused to move in one or more directions (e.g., up and down, left and right, forward and backward). In some embodiments, the processing device 140 may determine, based on the AR image (or video), an offset between a current position of the table (captured in at least one of the at least two images) and the target position of the table by comparing the position of the real contour profile of the table and the position of the virtual contour profile of the table in the AR image. In some embodiments, the processing device 140 may display the offset in the display device for the operator's reference. In some embodiments, the operator may press (or operate) the operating keys (or buttons, handles) based on the AR image and the offset.

In some embodiments, the processing device 140 may cause the table to be automatically moved to the target position of the table based on the AR image. In some embodiments, after generating the AR image, the processing device 140 may determine, based on the AR image, an offset between a current position of the table (captured in at least one of the at least two images) and the target position of the table by comparing at least a portion of the second set of elements corresponding to the table (e.g., the real contour profile of the table) and the (virtual) contour profile of the table. In some embodiments, the portion of the second set of elements corresponding to the table may represent the real contour profile of the table at the current position. In some embodiments, the processing device 140 may cause the table to move to the target position of the table based on the offset. In some embodiments, if the offset is greater than a threshold, the processing device 140 (e.g., the control unit 420) may cause the table to move; if the offset is smaller than the threshold (which indicates that the real contour profile of the table may be considered coincident with the virtual contour profile of the table), the processing device 140 (e.g., the control unit 420) may cause the table to stop moving. In some embodiments, the threshold may be set according to a default setting of the system 100 or preset by a user or operator via the terminal 130. It should be noted that, in response to a determination that the offset is equal to the threshold, the processing device 140 may either cause the table to move or cause the table to stop moving. In some embodiments, the processing device 140 (e.g., the display unit 460) may display a notification indicating that the table has been positioned at the target position.

It should be noted that the above description of the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 500 may further include an operation for determining the target position of the table. The target position of the table may be predetermined based on position information of a contour profile of the table determined in the treatment plan. As another example, in 508, the processing device 140 may project a virtual surface of the object (more descriptions of the virtual surface of the object may be found elsewhere in the present disclosure (e.g., FIG. 6 and descriptions thereof)) onto the 3D image so that the operator may observe the virtual surface of the object in the AR image. As a further example, the processing device 140 may determine whether to project the virtual contour profile of the table and/or the virtual surface of the object onto the 3D image according to instruction(s) of the operator. As still a further example, the operation 510 may be omitted.

Figure 6:
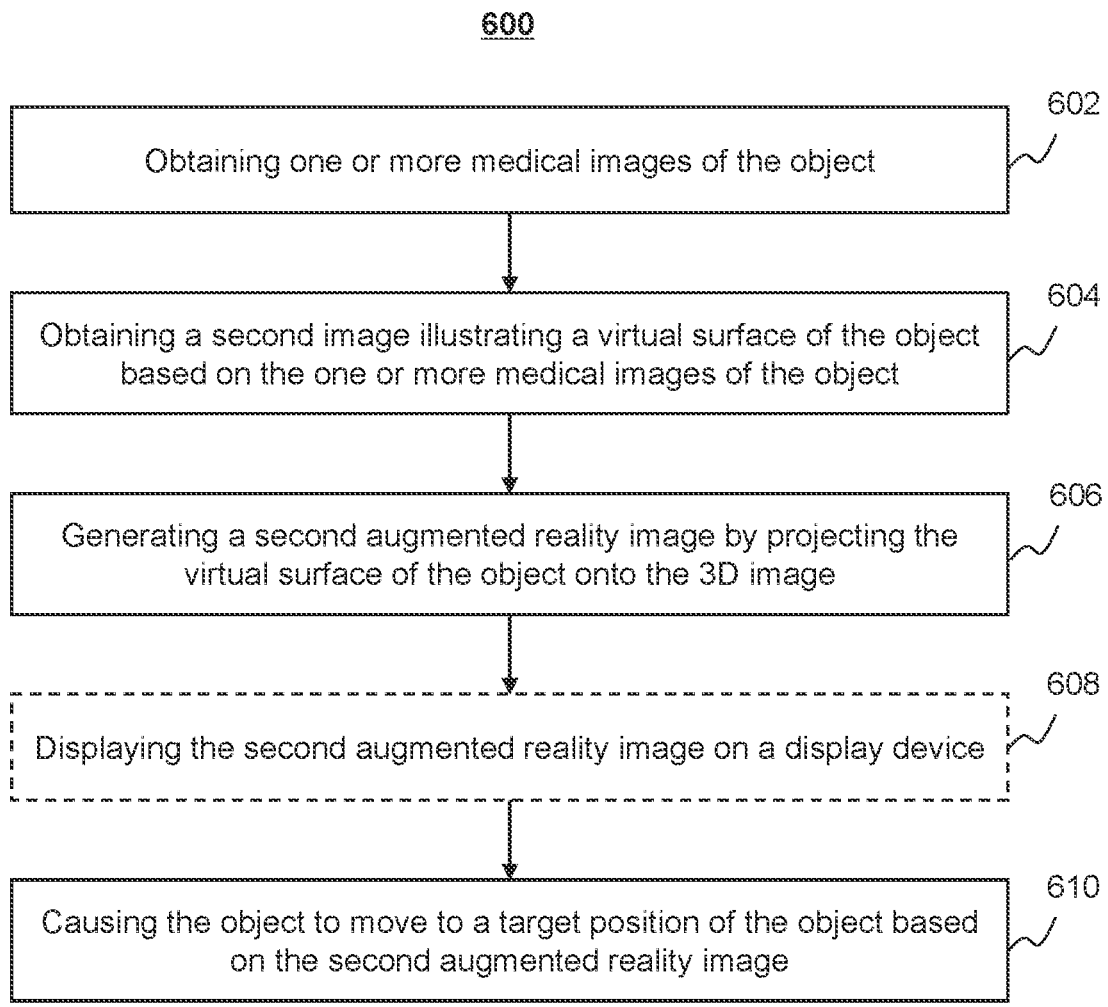
FIG. 6 is a flowchart illustrating an exemplary process for positioning an object positioned on a table according to some embodiments of the present disclosure.

FIG. 6 is a flowchart illustrating an exemplary process for positioning an object positioned on a table according to some embodiments of the present disclosure. In some embodiments, at least part of process 600 may be performed by the processing device 140 (implemented in, for example, the computing device 200 shown in FIG. 2). For example, the process 600 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting. In some embodiments, at least a portion of the operations in the process 600 may be performed before, after, or between, or simultaneously with one or more operations of the process 500.

In 602, one or more medical images of the object may be obtained. In some embodiments, the medical images may include one or more tomography images of the object. The one or more tomography images of the object may be obtained by the processing device 140 (e.g., the acquisition unit 410). In some embodiments, the object may be a patient or a portion of the patient. In some embodiments, the tomography image(s) may include one or more computed tomography (CT) images, one or more magnetic resonance (MR) images, one or more ultrasound images, or the like, or any combination thereof. In some embodiments, the tomography image(s) may be generated in an imaging process before the positioning process illustrated in FIGS. 5 and 6. For example, the tomography image(s) may be generated before treatment planning, and the tomography image(s) may provide an anatomical structure of the internal organs of the object as a reference for the treatment planning. In some embodiments, the generated tomography image(s) may be stored in the storage device 150, and the processing device 140 may obtain the tomography image(s) from the storage device 150.

In 604, a second image illustrating a virtual surface (or profile) of the object may be obtained based on the one or more medical images of the object. The second image may be obtained by the processing device 140 (e.g., the control unit 420). In some embodiments, the tomography image(s) obtained in 602 may be 2D slice images of the object in a traverse plane, a coronal plane, a sagittal plane or a plane with any inclination angle in a 3D space. In some embodiments, the tomography image(s) may form volume data of the object (or a portion thereof (e.g., the head of the object, a chest of the object, an abdomen of the object, etc.)). In some embodiments, the second image may be a virtual 3D image, for example, a virtual 3D CT image, of the object generated based on the tomography image(s). In some embodiments, the processing device 140 may adjust the window widths (WW) and/or window levels (WL) of the second image, so that the second image may illustrate the virtual surface (or profile) of the object. In some embodiments, the virtual surface of the object may be represented by a virtual contour profile of the object and/or region(s) within the virtual contour profile of the object. In some embodiments, the virtual contour profile of the object may be an edge of the virtual surface of the object.

In 606, a second AR image may be generated by projecting the virtual surface of the object onto the 3D image. The second AR image may be generated by the processing device (e.g., the projection unit 450). In some embodiments, as illustrated in FIG. 5, the 3D image may include the first set of elements (e.g., pixels) corresponding to the object and the second set of elements (e.g., pixels) corresponding to the table. In some embodiments, the first set of elements may represent a real contoured surface (or profile) of the object. In some embodiments, the second AR image generated by projecting the virtual surface of the object onto the 3D image may include the first set of elements representing the real contoured surface (or profile) of the object and the virtual surface of the object. In some embodiments, the second AR image may be generated by projecting the virtual surface of the object onto an AR image generated in the process 500. In some embodiments, the processing device 140 may determine whether to project the virtual contour profile of the table and/or the virtual surface of the object onto the 3D image according to instruction(s) of the operator.

In 608, the second AR image may be displayed on a display device (e.g., the display device described in 510). The second AR image may be displayed by the processing device 140 (e.g., the display unit 460). More descriptions of the display device may be found elsewhere in the present disclosure (e.g., FIG. 5 and the descriptions thereof).

In 610, the object may be caused to move to a target position of the object based on the second AR image. The object may be caused to move by the processing device 140 (e.g., the control unit 420). In some embodiments, the target position of the object (or a portion thereof) may be predetermined in the treatment plan, for example, during treatment planning, a target portion (e.g., the head, the chest, the abdomen, etc.) of the object may be positioned at the target position. In some embodiments, because the target positions of the object relative to the table are specified and identical during the treatment planning process and the positioning process, the virtual (contour) surface (or profile) of the object and the real contoured surface (or profile) of the object may be represented in the same coordinate system. The target position of the object may correspond to a position that the real contoured surface (or profile) of the object is coincident with the virtual (contour) surface (or profile) of the object. Therefore, if the real contoured surface (or profile) of the object is coincident with the virtual (contour) surface (or profile) of the object, the object may be considered to have arrived at the target position.

In some embodiments, the object may be caused to move by an operator. For example, based on the second AR image displayed on the display device, the operator may determine whether the real contoured surface (or profile) of the object is coincident with the virtual (contour) surface (or profile) of the object. If the operator determines that the real contoured surface (or profile) of the object is not coincident with the virtual (contour) surface (or profile) of the object, the operator may interact with the object and cause the object to move to the target position (additionally or alternatively the operator may directly move the object to the target position). If the operator determines that the real contoured surface (or profile) of the object is coincident with the virtual (contour) surface (or profile) of the table, the positioning process may be terminated. In some embodiments, the processing device 140 may determine, based on the second AR image (or video) a second offset between a current position of the object (captured in at least one of the at least two images) and the target position of the object by comparing the position of the real contoured surface (or profile) of the object and the position of the virtual (contour) surface (or profile) of the object in the second AR image. In some embodiments, the processing device 140 may display the second offset in the display device for the operator's reference.

In some embodiments, the processing device 140 may cause the object to be automatically moved to the target position of the object based on the second AR image. In some embodiments, the object may lie on the tabletop of the table. In some embodiments, the processing device 140 may cause the tabletop to move relative to the table (e.g., the base of the table). In some embodiments, after generating the second AR image, the processing device 140 may determine, based on the second AR image, a second offset between a current position of the object (captured in at least one of the at least two images) and the target position of the object by comparing at least a portion of the first set of elements corresponding to the object (e.g., the real contoured surface (or profile) of the object) and the virtual (contour) surface (or profile) of the object. In some embodiments, the portion of the first set of elements corresponding to the object may represent the real contoured surface (or profile) of the object at the current position. In some embodiments, the processing device 140 may cause the tabletop to move based on the second offset so that the object is located at the target position of the object. In some embodiments, if the second offset is greater than a threshold, the processing device 140 (e.g., the control unit 420) may cause the tabletop to move; if the second offset is smaller than the threshold (which indicates that the real contoured surface (or profile) of the object may be deemed to be coincident with the virtual (contour) surface (or profile) of the object), the processing device 140 (e.g., the control unit 420) may cause the tabletop to stop moving. In some embodiments, the threshold may be set according to a default setting of the system 100 or preset by a user or operator via the terminal 130. It should be noted that, in response to a determination that the second offset is equal to the threshold, the processing device 140 may either cause the tabletop to move or cause the tabletop to stop moving. In some embodiments, the processing device 140 (e.g., the display unit 460) may display a notification indicating that the object has been positioned at the target position.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 608 may be omitted. In some embodiments, the processing device 140 may cause the capture devices 160 to capture the images of the table and/or the object continuously, and the processing device 140 may generate a stream of AR images (e.g., an AR video).

Figure 7:
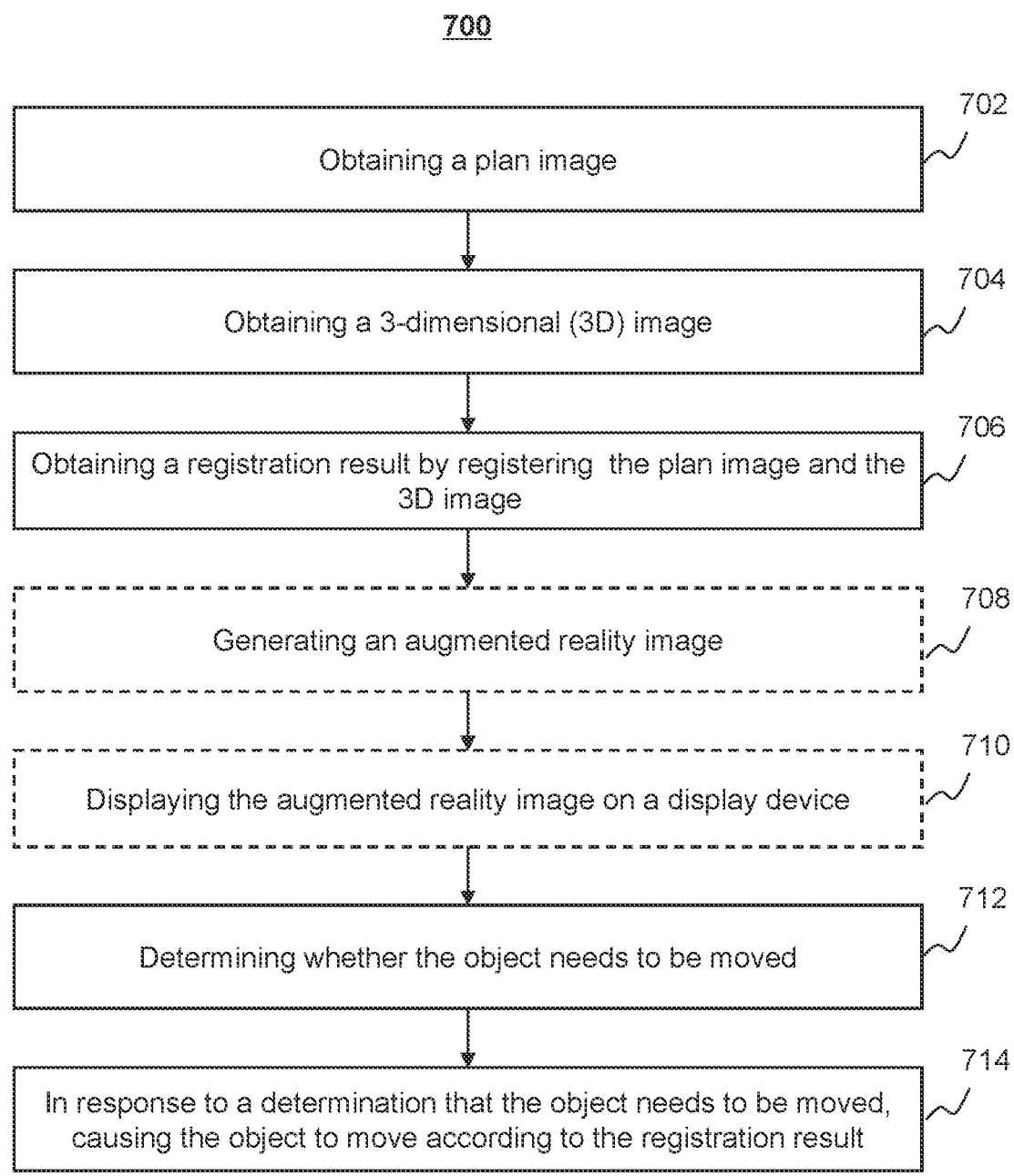
FIG. 7 is a flowchart illustrating an exemplary process for positioning an object positioned on a table according to some embodiments of the present disclosure.

FIG. 7 is a flowchart illustrating an exemplary process for positioning an object positioned on a table according to some embodiments of the present disclosure. In some embodiments, at least part of process 700 may be performed by the processing device 140 (implemented in, for example, the computing device 200 shown in FIG. 2). For example, the process 700 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In some embodiments, the process 700 may be performed before an imaging process or a treatment process to position an object supported on a table of the apparatus 110, such that a target portion of the object may be located at (or in the vicinity of) an imaging isocenter of an imaging device or a treatment isocenter of a radiotherapy device. After the object is positioned, the imaging process or the treatment process may be performed. For example, after the object is positioned, the object may be treated by radiation rays generated by an RT device. As another example, after the object is positioned, the object may be scanned by a CT imaging device to generate an image (e.g., a scout image) of the object. In some embodiments, because the object is supported on the table, the table may be positioned first, and then the position of the object may be adjusted relative to the table. In some embodiments, the position of the object relative to the table may be adjusted first, and then the table may be positioned. A positioning process for radiation treatment described below is merely provided for the purposes of illustration, and not intended to limit the scope of the present disclosure. A positioning process for imaging may be made under the teachings of the present disclosure.

In 702, a plan image may be obtained. The plan image may illustrate a virtual surface of the object. The plan image illustrating the virtual surface of the object may be obtained by the processing device 140 (e.g., the acquisition unit 410). In some embodiments, the virtual surface of the object may be represented by a virtual contour profile of the object and/or one or more regions within the virtual contour profile of the object. In some embodiments, the one or more regions may include one or more (or all) regions of interest within the virtual contour profile of the object. In some embodiments, the virtual contour profile of the object may be an edge of the virtual surface of the object. In some embodiments, the plan image the may be obtained based on the one or more tomography images of the object. More descriptions of the plan image illustrating the virtual surface of the object may be found elsewhere in the present disclosure (e.g., FIG. 6 and the descriptions thereof).

In 704, a 3-dimensional (3D) image may be obtained. The 3D image may include a set of elements (e.g., pixels) corresponding to the object. The 3D image including the set of elements (e.g., pixels) corresponding to the object may be obtained by the processing device (e.g., the acquisition unit 410). In some embodiments, the set of elements included in the 3D image may represent a real contoured surface (or profile) of the object. In some embodiments, the 3D image may be generated based on at least two images captured (or generated) by one or more capture devices (e.g., the first capture device 161 and the second capture device 162). In some embodiments, at least one of the one or more capture devices may be a depth camera. More descriptions of generating the 3D image may be found elsewhere in the present disclosure (e.g., FIGS. 5 and 6 and the descriptions thereof).

In 706, a registration result may be obtained by registering the plan image and the 3D image. The registration result may be obtained by the processing device 140 (e.g., the registration unit 430). In some embodiments, the registration result includes a rotation matrix and/or a translation matrix. The rotation matrix may represent a conversion relationship between the coordinate system of the plan image and the coordinate system of the 3D image. Through the rotation matrix, elements in the plan image may be transformed into the coordinate system of the 3D image. The translation matrix may represent a translation amount of the plan image to align the virtual (contour) surface (or profile) of the object in the plan image with the real contoured surface (or profile) of the object in the 3D image. In some embodiments, the translation matrix may be a one-dimensional translation vector when the plan image is need to be translated in one dimensional to align the virtual (contour) surface (or profile) of the object in the plan image with the real contoured surface (or profile) of the object in the 3D image. For example, the plan image may be provided in the DICOM coordinate system. The 3D image may be provided in the IEC coordinate system. A rotation matrix X may be determined representing the conversion relationship between the DICOM coordinate system and the IEC coordinate system. Element $A_1$ may represent a specific point (e.g., right eye of a patient) in the virtual surface of the object in the plan image. Element $A_2$ may represent the specific point in the real surface of the object in the 3D image. The Element $A_1$ may be transform into the IEC coordinate system by multiplying the rotation matrix X. The transformed Element $A_1$ may correspond to an element A' in the IEC coordinate system. A translation matrix B may be determined based on the element $A_2$ and the element A in the IEC coordinate system. According to the rotation matrix X and the translation matrix B, an element of the plan image in DICOM coordinate system may be transformed and translated to correspond an element of the 3D image in the IEC coordinate system.

In 708, an AR image may be generated. The AR image may be generated by projecting the virtual surface of the object onto the 3D image. The AR image may be generated by the processing device 140 (e.g., the projection unit 450). In some embodiments, the processing device 140 may fuse the plan image and the 3D image to generate the AR image. The plan image may include the virtual (contour) surface (or profile) of the object. In some embodiments, the 3D image may include the set of elements corresponding to the object. The set of elements may represent the real contoured surface (or profile) of the object. Therefore, the AR image generated by projecting the virtual (contour) surface (or profile) of the object onto the 3D image may include the set of elements representing the real contoured surface (or profile) of the object and the virtual surface of the object.

In 710, the AR image may be displayed on a display device. The AR image may be displayed by the processing device 140 (e.g., the display unit 460). In some embodiments, the display unit 460 may include a video display (e.g., an electroluminescent display, an electronic paper, alight-emitting diode (LED) display, a liquid crystal display (LCD), a plasma display, a digital micromirror device (DMD), a liquid on silicon display, a field emission display, a laser color video display, a quantum dot display, an interferometric modulator display, a flexible display, etc.), a non-video display (e.g., a vacuum fluorescent display, a seven segment display, etc.), a 3D display (e.g., a holographic display, a retina display, a fog display, etc.), or the like, or a combination thereof. An exemplary display may be a head mounted display (HMD), a display device (e.g., a flat panel display or a curved panel display), or the like. In some embodiments, an operator can observe the AR image from the display device. In some embodiments, the AR image may be directly displayed on the table and/or the RT apparatus to guide an operation, e.g., positioning of the object by, e.g., the object himself or with the assistance of the operator.

In 712, a determination of whether the object needs to be moved may be made based on the registration result. The determination may be determined by the processing device 140 (e.g., the control unit 420). In some embodiments, as described in connection with 706, the registration result may include the translation matrix. The translation matrix may represent the translation amount of the plan image to align the virtual (contour) surface (or profile) of the object in the plan image with the real contoured surface (or profile) of the object in the 3D image. In other words, the translation amount may correspond to an offset between a first position of the object in the 3D image and a second position of the object in the plan image. The offset may be further compared with a threshold to determine whether the object needs to be moved. In some embodiments, if the offset is greater than the threshold, the processing device 140 (e.g., the control unit 420) may determine that the object needs to be moved; if the offset is smaller than the threshold (which indicates that the real contoured surface (or profile) of the object is deemed to coincide with the virtual (contour) surface (or profile) of the object), the processing device 140 (e.g., the control unit 420) may determine that the object does not need to be moved. In some embodiments, the threshold may be set according to a default setting of the system 100 or set by a user or operator via the terminal 130.

In 714, the object may be caused to move according to the registration result in response to a determination that the object needs to be moved. The object may be caused to move by the processing device 140 (e.g., the control unit 420). In some embodiments, as described in connection with 712, the registration result may include the translation matrix, based on which the offset between first position of the object in the 3D image and the second position of the object in the plan image may be determined. The object may be caused to move according to the offset. In some embodiments, the object may be caused to move by or with the assistance of an operator. In some embodiments, the processing device 140 may cause the object to be automatically moved. More descriptions of the process of causing the object to move may be found elsewhere in the present disclosure (e.g., FIGS. 5 and 6 and the descriptions thereof).

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 708 and 710 may be omitted. In some embodiments, the processing device 140 may cause the capture devices 160 to capture a series of images of the table and/or the object (e.g., continuously), and the processing device 140 may generate a stream of AR images (e.g., an AR video).

Figure 8:
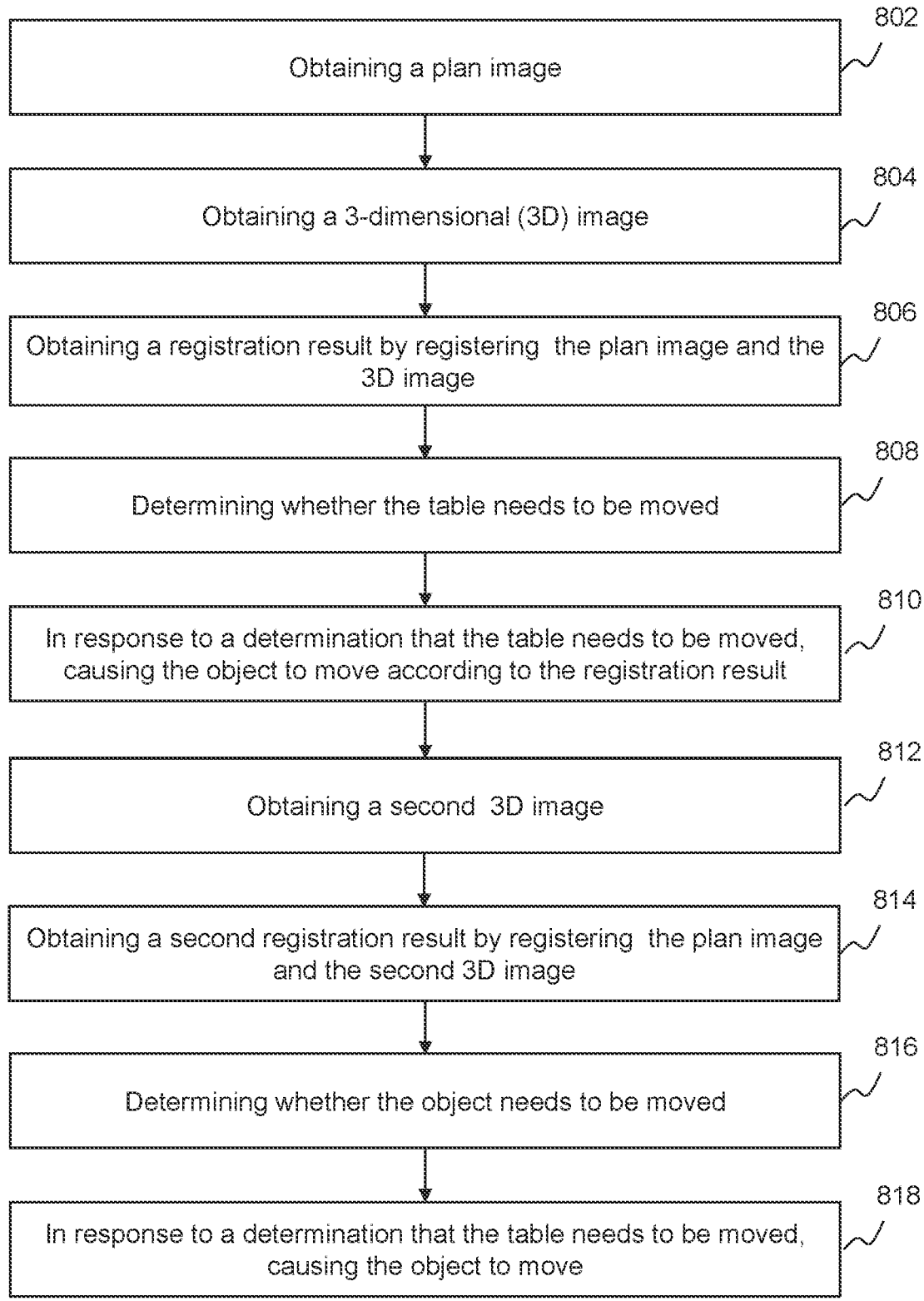
FIG. 8 is a flowchart illustrating an exemplary process for positioning an object positioned on a table according to some embodiments of the present disclosure.

FIG. 8 is a flowchart illustrating an exemplary process for positioning an object positioned on a table according to some embodiments of the present disclosure. In some embodiments, at least part of process 800 may be performed by the processing device 140 (implemented in, for example, the computing device 200 shown in FIG. 2). For example, the process 800 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

In some embodiments, the process 800 may be performed before an imaging process or a treatment process to position an object supported on a table of the apparatus 110, such that a target portion of the object may be located at (or in the vicinity of) an imaging isocenter of an imaging device or a treatment isocenter of a radiotherapy device. After the object is positioned, the imaging process or the treatment process may be performed. For example, after the object is positioned, the object may be treated by radiation rays generated by an RT device. As another example, after the object is positioned, the object may be scanned by a CT imaging device to generate an image (e.g., a scout image) of the object. In some embodiments, because the object is supported on the table, the table may be positioned first, and then the position of the object may be adjusted relative to the table. In some embodiments, the position of the object relative to the table may be adjusted first, and then the table may be positioned. A positioning process for radiation treatment described below is merely provided for the purposes of illustration, and not intended to limit the scope of the present disclosure. A positioning process for imaging may be made under the teachings of the present disclosure.

In 802, a plan image may be obtained. The plan image may including a contour profile of the table determined in a treatment plan and a virtual surface of the object. The plan image may be obtained by the processing device (e.g., the acquisition unit 410). In some embodiments, the contour profile of the table determined in the treatment plan may be a virtual contour profile. In some embodiments, the virtual surface of the object may be represented by a virtual contour profile of the object and/or region(s) within the virtual contour profile of the object. In some embodiments, the virtual contour profile of the object may be an edge of the virtual surface of the object. In some embodiments, the plan image may be obtained based on the one or more tomography images of the object.

In 804, a 3-dimensional (3D) image may be obtained. The 3D image may be obtained by the processing device (e.g., the acquisition unit 410). In some embodiments, the 3D image may include a first set of elements (e.g., pixels) corresponding to the object and a second set of elements (e.g., pixels) corresponding to the table. In some embodiments, the first set of elements corresponding to the object may represent the object in the 3D image. The second set of elements corresponding to the table may represent the table in the 3D image. More descriptions of the 3D image may be found elsewhere in the present disclosure (e.g., FIGS. 5-7 and the descriptions thereof).

In 806, a registration result may be obtained by registering the plan image and the 3D image. The registration result may be obtained by the processing device 140 (e.g., the registration unit 430). In some embodiments, the registration result includes a rotation matrix and/or a translation matrix. The rotation matrix may represent a conversion relationship between the coordinate system of the plan image and the coordinate system of the 3D image. The translation matrix may represent a translation amount of the plan image to make the virtual (contour) surface (or profile) of the object in the plan image being coincident with the real contoured surface (or profile) of the object in the 3D image. More descriptions of the registration result may be found elsewhere in the present disclosure (e.g., FIG. 7 and the descriptions thereof).

In 808, a determination of whether the table needs to be moved may be made based on the registration result. The determination may be determined by the processing device 140 (e.g., the control unit 420). In some embodiments, the processing device 140 (e.g., the control unit 420) may first determine an first offset between a first position of the object in the 3D image and a second position of the object in the plan image based on the registration result. In some embodiments, if a first relative distance between the object and the table in the plan image is deemed to be equal to a second relative distance between the object and the table in the 3D image, the first offset may be determined to be equal to a second offset between the a third position of the table in the 3D image and a fourth position of the table in the plan image. In some embodiments, if the first relative distance between the object and the table in the plan image is deemed to be not equal to a second relative distance between the object and the table in the 3D image, the processing device 140 (e.g., the control unit 420) may determine the second offset based on the the first offset, the first relative distance, and the second relative distance. Further, the processing device 140 (e.g., the control unit 420) may determine whether the table needs to be moved by comparing the second offset with a threshold. In some embodiments, if the second offset is greater than the threshold, the processing device 140 (e.g., the control unit 420) may determine that the table needs to be moved; if the second offset is smaller than the threshold, the processing device 140 (e.g., the control unit 420) may determine that the table does not need to be moved.

In 810, the table may be caused to move according to the registration result in response to a determination that the table needs to be moved. The table may be caused to move by the processing device 140 (e.g., the control unit 420). In some embodiments, the registration result may include the translation matrix, based on which the second offset between the third position of the table in the 3D image and the fourth position of the table in the plan image may be determined. The table may be caused to move according to the second offset. In some embodiments, the table may be caused to move by an operator. In some embodiments, the processing device 140 may cause the table to be automatically moved. More descriptions of the process of causing the object to move may be found elsewhere in the present disclosure (e.g., FIGS. 5 and 6 and the descriptions thereof).

In 812, a second 3D image may be obtained. The second 3D image may be obtained by the processing device 140 (e.g., the acquisition unit 410). In some embodiments, the second 3D image may be obtained after the table is moved according to the registration result. In some embodiments, the second 3D image may include a third set of elements (e.g., pixels) corresponding to the object and a fourth set of elements (e.g., pixels) corresponding to the table. In some embodiments, the third set of elements included in the second 3D image may represent a real contoured surface (or profile) of the object. In some embodiments, the fourth set of elements included in the second 3D image may represent a real contour profile of the table.

In 814, a second registration result may be obtained by registering the plan image with the second 3D image. The second registration result may be obtained by the processing device 140 (e.g., the registration unit 430). In some embodiments, the second registration result includes a second rotation matrix and/or a second translation matrix. The second rotation matrix may represent the conversion relationship between the coordinate system of the plan image and the coordinate system of the second 3D image. The translation matrix may represent a second translation amount of the plan image to make the virtual (contour) surface (or profile) of the object in the plan image being coincident with the real contoured surface (or profile) of the object in the second 3D image.

In 816, a determination of whether the object needs to be moved may be made based on the registration result. The determination may be made by the processing device 140 (e.g., the control unit 420). In some embodiments, the processing device 140 (e.g., the control unit 420) may determine an third offset between a fifth position of the object in the second 3D image and the second position of the object in the plan image based on the registration result. In some embodiments, if the second offset is determined to be equal to the first offset, the virtual (contour) surface (or profile) of the object in the plan image may coincide with the real contoured surface (or profile) of the object in the second 3D image after the moving of the table according to the second offset. In this situation, the third offset may be zero. In some embodiments, if the second offset is determined to be not equal to the first offset, the virtual (contour) surface (or profile) of the object in the plan image may not coincide with the real contoured surface (or profile) of the object in the second 3D image after the moving of the table according to the second offset. In this situation, the third offset may be determined by comparing at least a portion of the third set of elements corresponding to the object in the second 3D image and the virtual (contour) surface (or profile) of the object in the plan image. Further, the processing device 140 (e.g., the control unit 420) may determine whether the object needs to be moved by comparing the third offset with a second threshold. In some embodiments, if the third offset is greater than the second threshold, the processing device 140 (e.g., the control unit 420) may determine that the object needs to be moved; if the third offset is smaller than the second threshold, the processing device 140 (e.g., the control unit 420) may determine that the object does not need to be moved.

In 818, the object may be caused to move according to the registration result in response to a determination that the object needs to be moved. The object may be caused to move by the processing device 140 (e.g., the control unit 420). In some embodiments, the second registration result may include the second translation matrix, based on which the third offset between the fifth position of the object in the second 3D image and the second position of the object in the plan image may be determined. The object may be caused to move according to the third offset. In some embodiments, the object may be caused to move by an operator. In some embodiments, the processing device 140 may cause the object to be automatically moved. More descriptions of the process of causing the object to move may be found elsewhere in the present disclosure (e.g., FIGS. 5 and 6 and the descriptions thereof).

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 808 and 810 may be combined into one operation. In some embodiments, the processing device 140 may cause the capture devices 160 to capture the images of the table and/or the object continuously, and the processing device 140 may generate a stream of AR images (e.g., an AR video).

Figure 9:
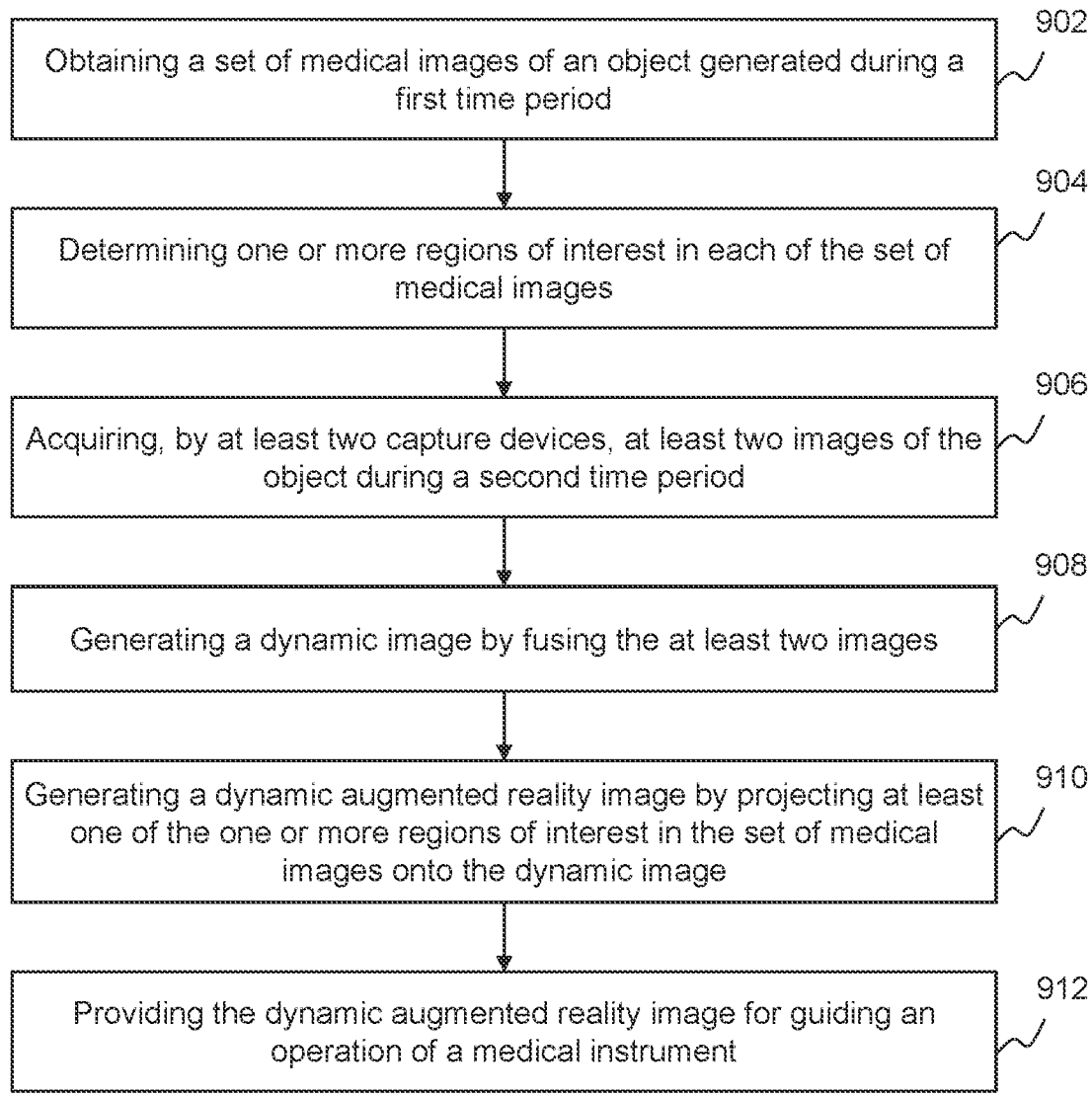
FIG. 9 is a flowchart illustrating an exemplary process for guiding an operation of a medical instrument during a medical procedure according to some embodiments of the present disclosure.

FIG. 9 is a flowchart illustrating an exemplary process for guiding an operation of a medical instrument during a medical procedure according to some embodiments of the present disclosure. In some embodiments, at least part of process 900 may be performed by the processing device 140 (implemented in, for example, the computing device 200 shown in FIG. 2). For example, the process 900 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, a set of medical images of an object generated during a first time period may be obtained. The set of medical images of the object may be obtained by the processing device 140 (e.g., the acquisition unit 410). In some embodiments, the object may be a patient or a portion of the patient. In some embodiments, the set of medical images of the object may include computed tomography (CT) images, magnetic resonance (MR) images, ultrasound images, or the like, or any combination thereof. For example, the set of medical images may include four-dimensional (4D) CT images of the object. In some embodiments, the set of medical images of the object may be generated by the apparatus 110 before the process 900, and stored in the storage device 150. In some embodiments, the generation of the set of medical images of the object may also be referred to as a preoperative medical examination. In some embodiments, the processing device 140 may obtain the set of medical images of the object from the storage device 150 or the apparatus 110. In some embodiments, the first time period may include one or more motion cycles of the object. In some embodiments, the motion may include a physiological motion of the object, for example, respiratory motion, cardiac motion, muscle contraction and relaxation, etc. In some embodiments, the first time period may include a respiratory motion cycle with a duration of approximately 4 seconds.

In 904, one or more regions of interest in one or more (e.g., each) of the set of medical images may be determined. The regions of interest may be determined by the processing device 140 (e.g., the control unit 420). In some embodiments, the region(s) of interest may include a target region of the object that will be processed (or treated) by a medical instrument during a medical procedure. In some embodiments, the region(s) of interest may also include one or more regions around the target region. The medical procedure may include a surgery (e.g., an (image-guided) intervention or a biopsy procedure). The medical instrument may include a biopsy needle. The target region may include an organ (e.g., a lung, a liver, a heart, etc.) or a portion thereof (e.g., a tumor, a nodule, bleeding spot, or the like, or any combination thereof). In some embodiments, the target region of the object may move with the motion of the object (e.g., respiratory motion, cardiac motion, muscle contraction and relaxation, etc.), and it may be difficult to identify the position of the target region. Therefore, the set of medical images of the object may be used to guide the operation of the medical instrument. In some embodiments, the region(s) of interest may be determined based on one or more image segmentation algorithms. Exemplary image segmentation algorithms may include threshold segmentation, region growing, watershed segmentation, morphological segmentation algorithm, statistics segmentation, or the like, or any combination thereof.

Merely by way of example, the set of medical images may be 4D CT images of the chest of the object, and a lung of the object may have a nodule. Therefore, a biopsy procedure may need to be conducted on the nodule to diagnose whether the nodule becomes malignant. The target region may include the nodule of the lung. The region(s) of interest in the set of chest 4D CT images may include the nodule, the lung, the ribs, the heart, a blood vessel in the vicinity of the nodule, etc. The region(s) of interest may be obtained by segmenting the set of chest 4D CT images using one or more image segmentation algorithms illustrated elsewhere in the present disclosure. Because the nodule may have greater gray values than that of normal lung tissue, the nodule may be segmented from the lung based on the difference in gray values.

In 906, at least two images of the object (and/or the medical instrument) during a second time period may be acquired. In some embodiments, the at least two images of the object may be acquired by the processing device 140 (e.g., the acquisition unit 410). In some embodiments, the at least two images of the object may be captured (or generated) by at least two capture devices (e.g., the first capture device 161, the second capture device 162). In some embodiments, each capture device of the at least two capture devices may capture one of the at least two images. In some embodiments, the at least two images of the object during the second time period may be real scene images (or dynamic images, or videos) of the object in different view angles. For example, the first capture device 161 and the second capture device 162 may capture the images of the object from different view angles (e.g., 45 degrees on the upper left and 45 degrees on the upper right, respectively). In some embodiments, the at least two images may include three-dimensional information (e.g., the contour or surface) of the object. In some embodiments, the 3D information of the object may include depth information that may be used to reconstruct the 3D surface of the object. In some embodiments, the at least two capture devices may capture at least two videos (or dynamic images) of the object during the second time period. The at least two images may be at least a portion of the frame images of the at least two videos (or dynamic images). In some embodiments, the at least two capture devices may automatically capture the images (or dynamic images, or videos) of the object during the medical procedure consistently, and the images (or dynamic images, or videos) may be transmitted to the processing device 140 and/or the storage device 150 in real time, such that the processing device 140 may obtain the images (or dynamic images, or videos). In some embodiments, the processing device 140 may transmit instruction(s) for capturing images (or dynamic images, or videos) of the object to the capture devices, such that the capture devices may capture the images (or dynamic images, or videos) and transmit the images (or dynamic images, or videos) to the processing device 140.

In some embodiments, the second time period may include one or more motion cycles of the object. In some embodiments, the motion may include a physiological motion of the object, for example, respiratory motion, cardiac motion, muscle contraction and relaxation, etc. In some embodiments, the second time period may include the duration of the medical procedure (or at least a portion thereof). In some embodiments, the second time period may have a larger duration than the first time period and a time starting point different from the first time period. For example, a preoperative medical examination (e.g., preoperative CT imaging) may be performed on the object from 8 a.m. to 8:30 a.m., and a surgery may be performed on the object from 2 p.m. to 5 p.m. The first time period may be from 8:10 a.m. to 8:20 a.m. with a duration of 10 minutes including about 150 respiratory cycles and a time starting point of 8:10 a.m. The second time period may be from 2:10 p.m. to 2:50 p.m. with a duration of 40 minutes including about 600 respiratory cycles and a time starting point of 2:10 p.m.

In 908, a dynamic image (or video) may be generated by fusing the at least two images (or dynamic images, or videos). The dynamic image may be generated by the processing device 140 (e.g., the reconstruction unit 440). In some embodiments, if the medical instrument is operated close to the object, the medical instrument may be presented in the dynamic image. In some embodiments, the processing device 140 may reconstruct the 3D image based on one or more image reconstruction algorithms (e.g., monocular vision algorithm, stereo vision algorithm, shape from shading algorithm, etc.). In some embodiments, the processing device 140 (e.g., the registration unit 430) may register the at least two images before reconstructing the 3D image based on the at least two images. In some embodiments, the processing device 140 (e.g., the registration unit 430) may register the at least two images (or a portion thereof) using one or more image registration algorithms (e.g., grayscale and template based registration algorithm, feature based registration algorithm, domain transformation based registration algorithm, etc.). In some embodiments, the processing device 140 may pre-process the at least two images before registering the at least two images. Exemplary pre-processing may include denoising, image enhancing, image segmentation, etc. In some embodiments, the processing device 140 may fuse each image frame of the video captured by the first capture device 161 with an image frame of the video captured by the second capture device 162, and generate the dynamic image (or video).

The dynamic image may include a set of elements corresponding to the object. In some embodiments, the dynamic image may be a fused 3D dynamic image (or a fused 3D video) of the object. In some embodiments, the processing device 140 may process the fused 3D dynamic image (or 3D video) of the object. For example, the processing device 140 may segment the fused 3D dynamic image (or 3D video), so that in the 3D dynamic image or the fused 3D video, the object may be extracted from background (e.g., the table). In some embodiments, a contoured surface (or profile) the object may be highlighted. In some embodiments, during the second time period, the set of elements corresponding to the contoured surface (or profile) of the object may change periodically with the motion of the object.

In 910, a dynamic AR image may be generated by projecting at least one of the one or more regions of interest in the set of medical images onto the dynamic image. In some embodiments, the at least one of the one or more regions of interest may include the target region of the object. In some embodiments, the dynamic AR image may present a real scene of the object (or a portion thereof), the at least one of the one or more regions of interest, and/or a real scene of the medical instrument, etc. The dynamic AR image may be generated by the processing device 140 (e.g., the projection unit 450). In some embodiments, the dynamic AR image may be a 3D dynamic AR image or a 3D AR video of the object. In some embodiments, the processing device 140 may identify the at least one of the one or more regions of interest in the set of medical images to be projected, and then project it onto the dynamic image fused in operation 908 to generate the dynamic AR image. In some embodiments, the processing device 140 may identify the at least one of the one or more regions of interest (e.g., the target region of the object) in the set of medical images to be projected based on one or more instructions of the operator. For example, the operator may select the at least one of the one or more regions of interest to be projected through a user interface implemented on the terminal 130, and the terminal 130 may send corresponding instructions to the processing device 140. In some embodiments, the processing device 140 (e.g., the registration unit 430) may register the at least one of the one or more regions of interest and the dynamic image in time and space. More descriptions of the projection operation may be found elsewhere in the present disclosure (e.g., FIG. 10 and the descriptions thereof). In some embodiments, the processing device 140 may fuse the at least one of the one or more regions of interest and the dynamic image to generate the dynamic AR image.

In 912, the dynamic AR image may be provided for guiding an operation of the medical instrument. As described above, the dynamic AR image may include the at least one of the one or more regions of interest. In some embodiments, the processing device 140 (e.g., the display unit 460) may display the dynamic AR image on a display device. More descriptions of the display device may be found elsewhere in the present disclosure (e.g., FIG. 5 and the descriptions thereof). In some embodiments, the operator may observe the dynamic AR image from the display device. In some embodiments, the operator may adjust a display effect of the dynamic AR image. For example, the operator may choose to zoom in or out, and/or drag the dynamic AR image, so that the operator may observe different portions (or scopes) of the object with different amplifications. The processing device 140 may receive instruction(s) associated with the display effect of the dynamic AR image from the operator and perform corresponding zooming in or out and/or dragging operations, or the like, to realize the display effect. In some embodiments, the operator may select or change the at least one of the one or more regions of interest to be projected onto the dynamic image, and accordingly, the processing device 140 may receive one or more instructions for selecting or changing the at least one of the one or more regions of interest to be projected onto the dynamic image and perform corresponding adjustment(s) in the dynamic AR image. In some embodiments, during the medical procedure, the operator may locate the at least one of the one or more regions of interest according to the dynamic AR image, and perform operation(s) of the medical instrument (e.g., biopsy needle). For example, the operator may observe, based on the dynamic AR image, in real time, whether an insertion position of the biopsy needle is close to the target region of the object, whether the needling direction (or puncture angle) is proper, and/or whether the puncture depth is proper, etc.

In some embodiments, the processing device 140 may automatically identify the target region of the object in the dynamic AR image based on one or more preset parameters (e.g., a puncture location) associated with the medical procedure. For example, if the medical procedure targets a lung nodule, the processing device 140 may automatically identify the target region of the object in which the lung nodule locates by segmenting the dynamic AR image (especially the at least one of the one or more regions of interest projected onto the dynamic image). In some embodiments, the processing device 140 may automatically determine a target position in the object for operating the medical instrument based on the positions of the pixels or voxels corresponding to the segmented target region of the object in the dynamic AR image. For example, the processing device 140 may determine a center position of the lung nodule as the target position. In some embodiments, the processing device 140 may determine a current puncture location of the biopsy needle, a current puncture angle of the biopsy needle, a current puncture depth of the biopsy needle, an offset between the target position in the object and the current puncture location of the biopsy needle, etc., based on the dynamic AR image. In some embodiments, the processing device 140 may display the information relating to the locations associated with the target region and the biopsy needle in the display device for the operator's reference, and guide the operation of the biopsy needle.

It should be noted that the above description of the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 900 may further include operations for generating control instructions, and/or transmitting the control instructions to the control unit 420 for generating one or more notifications to guide the operation of the medical instrument. As another example, after (or during) the medical instrument is operated according to the guidance of the dynamic AR image, a postoperative (or intraoperative) medical examination (e.g., an imaging process) may be performed to inspect the position of the medical instrument relative to the target region of the object.

Figure 10:
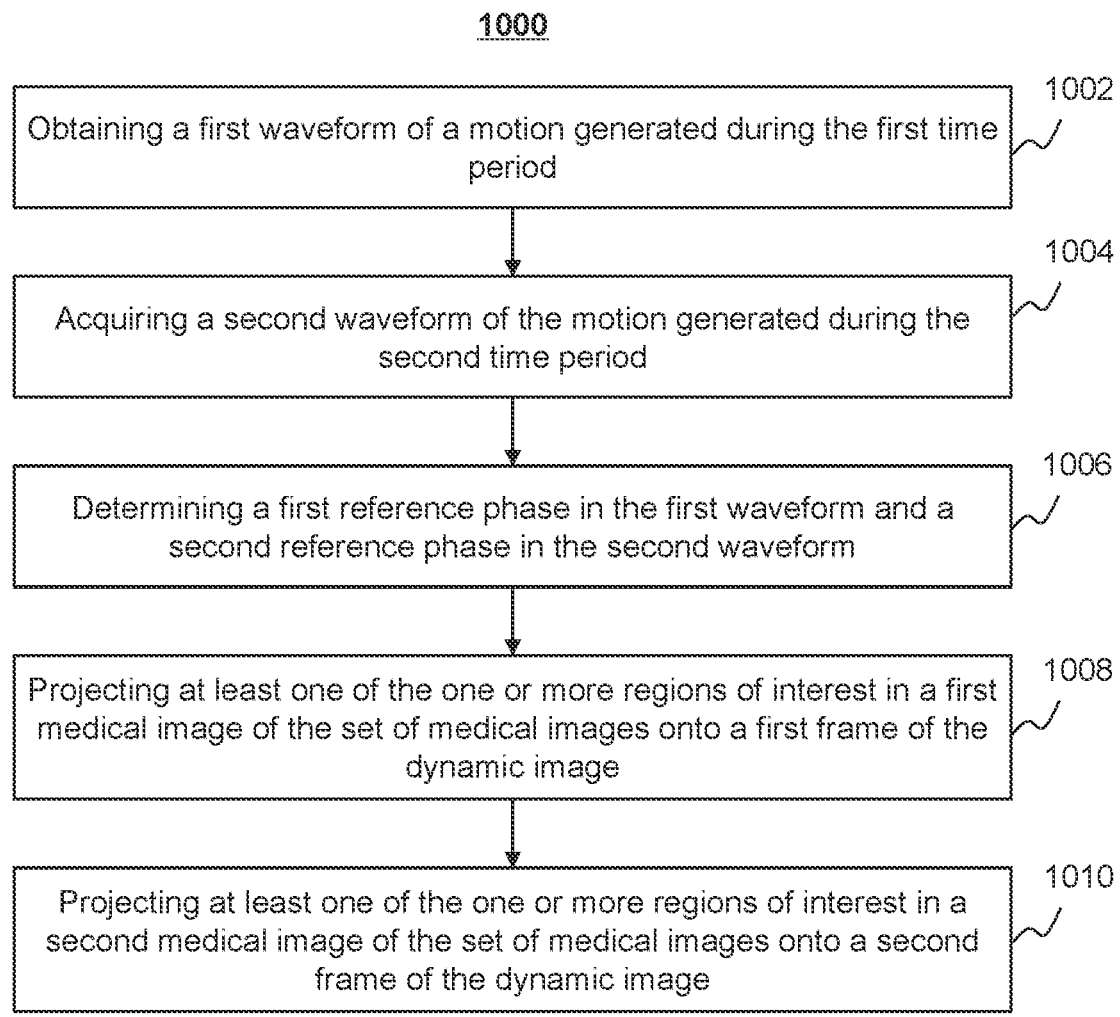
FIG. 10 is a flowchart illustrating an exemplary process for generating a dynamic augmented reality image according to some embodiments of the present disclosure.

FIG. 10 is a flowchart illustrating an exemplary process for generating a dynamic augmented reality image according to some embodiments of the present disclosure. In some embodiments, at least part of process 1000 may be performed by the processing device 140 (implemented in, for example, the computing device 200 shown in FIG. 2). For example, the process 1000 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 10 and described below is not intended to be limiting. In some embodiments, operation 910 illustrated in FIG. 9 may be performed according to the process 1000. In some embodiments, the processing device 140 (e.g., the registration unit 430) may register the region(s) of interest and the dynamic image in time and space in the generation of the dynamic AR image.

In 1002, a first waveform of a motion generated during the first time period may be obtained. The motion may refer to a physiological motion of the object illustrated elsewhere in the present disclosure. The first waveform of the motion may be obtained by the processing device 140 (e.g., the acquisition unit 410). Merely by way of example, the first waveform of the motion may be a respiratory waveform corresponding to the respiration of the object during the first time period. In some embodiments, the first waveform may be generated using a first physiological signal detection device (e.g., a respiratory monitor) during the first time period. For example, when preforming a preoperative CT imaging during the first time period, the first physiological signal detection device may be used to detect the first waveform during the first time period. In some embodiments, the first waveform may be simulated according to the dynamic image generated in 908. In some embodiments, the processing device 140 may obtain the first waveform of the motion from the storage device 150 or the first physiological signal detection device.

In 1004, a second waveform of the motion generated during the second time period may be acquired. The second waveform of the motion may be acquired by the processing device (e.g., the acquisition unit 410). In some embodiments, the second waveform of the motion may be a respiratory waveform corresponding to the respiration of the object during the second time period. In some embodiments, the second waveform may be generated using a second physiological signal detection device (e.g., a respiratory monitor) during the second time period. In some embodiments, the second physiological signal detection device may be the same as the first physiological signal detection device. In some embodiments, the processing device 140 may acquire the second waveform from the second physiological signal detection device. In some embodiments, the processing device 140 may generate the second waveform based on the motion amplitudes of the surface of the object during the second time period by analyzing the dynamic image generated in 908.

In 1006, a first reference phase in the first waveform and a second reference phase in the second waveform may be determined. The first reference phase and the second reference phase may be determined by the processing device 140 (e.g., the control unit 420). In some embodiments, a first characteristic phase (e.g., a phase with a minimum motion amplitude, or a phase with a maximum motion amplitude) in the first waveform may be designated as the first reference phase in the first waveform. In some embodiments, a second characteristic phase (e.g., a phase with a minimum motion amplitude, or a phase with a maximum motion amplitude) in the second waveform may be designated as the second reference phase in the second waveform. In some embodiments, the first waveform and the second waveform may not be exactly the same, which suggests the presence of a small error. Nevertheless, the first waveform and the second waveform may still be considered consistent if the error is small enough. In some embodiments, the first waveform and the second waveform may be registered in time based on the first reference phase and the second reference phase.

In 1008, at least one of the one or more regions of interest in a first medical image of the set of medical images may be projected onto (or registered with) a first frame of the dynamic image (e.g., the dynamic image generated in 908). Operation 1008 may be performed by the processing device 140 (e.g., the projection unit 450). In some embodiments, the first medical image may be generated at a first time point corresponding to the first reference phase. In some embodiments, the first frame may be generated at a second time point corresponding to the second reference phase. For example, the first reference phase (denoted as $\varphi_1$) may be the phase with a minimum motion amplitude in the first waveform corresponding to a time point $T_1$. Then the first medical image may be the image generated at the time point $T_1$. In some embodiments, each frame of the dynamic image may be a 3D image of the object. Similarly, the second reference phase (denoted as $\varphi_2$) may be the phase with a minimum motion amplitude in the second waveform corresponding to a time point $T_2$. Then the first frame of the dynamic image may be the image generated at the time point $T_2$. In some embodiments, the processing device 140 may register the first medical image and the first frame of the dynamic image before projecting the at least one of the one or more regions of interest in the first medical image onto the first frame of the dynamic image.

In 1010, at least one of the one or more regions of interest in a second medical image of the set of medical images may be projected onto a second frame of the dynamic image (e.g., the dynamic image generated in 908). Operation 1010 may be performed by the processing device 140 (e.g., the projection unit 450). In some embodiments, the second medical image may be generated at a third time point corresponding to a third phase. In some embodiments, the second frame may be generated at a fourth time point corresponding to a fourth phase. In some embodiments, the phase difference between the first reference phase at the first time point and the third phase at the third time point may be the same as the phase difference between the second reference phase at the second time point and the fourth phase at the fourth time point. For example, the second medical image may be the image generated at the time point $T_3$ corresponding to a third phase s. The second frame of the dynamic image may be the image generated at the time point $T_4$ corresponding to a fourth phase $\varphi_4$. The phase difference $\Delta\varphi_{1,3}$ between the phases $\varphi_1$ and $\varphi_3$ may be equal to the phase difference $\Delta\varphi_{2,4}$ between the phases $\varphi_2$ and $\varphi_4$. In some embodiments, the processing device 140 may register the second medical image and the second frame of the dynamic image before projecting the at least one of the one or more regions of interest in the second medical image onto the second frame of the dynamic image. Similarly, the other medical images of the set of medical images and the other frames of the dynamic image may be registered in time and space. In some embodiments, the processing device 140 may register the medical image(s) and the frame(s) of the dynamic image in space using one or more image registration algorithms (e.g., grayscale and template based registration algorithm, feature based registration algorithm, domain transformation based registration algorithm, etc.).

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 1000 may further include operations for determining a generation time point for each medical image in the set of medical images, and/or a corresponding time point for each frame in the dynamic image. In some embodiments, the projection unit 450 may perform the projection operation based on the generated time points and the corresponding time points. In some embodiments, the dynamic image in each motion cycle of the second time period may be registered with at least a portion of the set of medical images in a motion cycle of the first time period in this way, and the set of medical images may be reused in the projection process.

Figure 11:
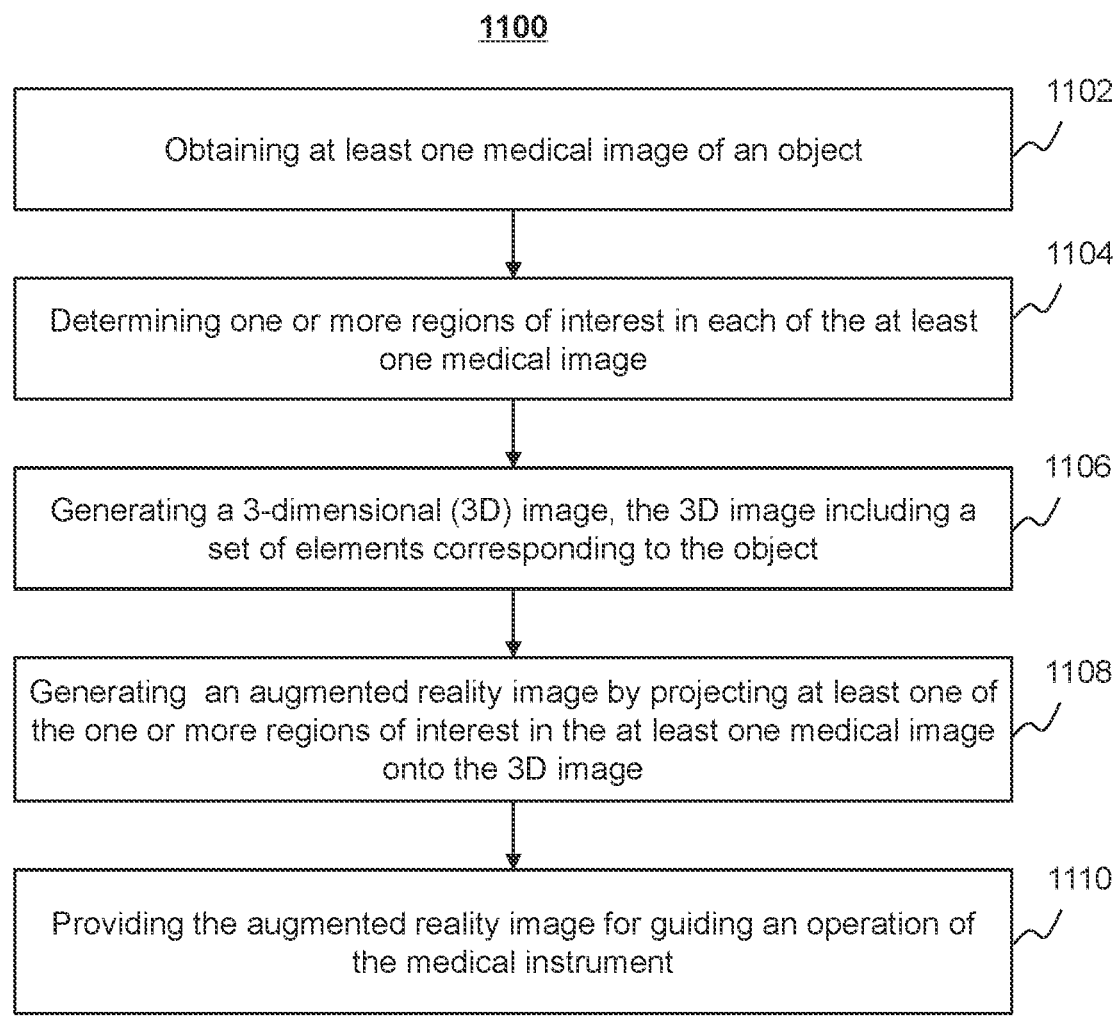
FIG. 11 is a flowchart illustrating an exemplary process for guiding an operation of an instrument during a procedure according to some embodiments of the present disclosure.

FIG. 11 is a flowchart illustrating an exemplary process for guiding an operation of an instrument during a procedure according to some embodiments of the present disclosure. In some embodiments, the procedure may be an imaging procedure or a treatment procedure. In some embodiments, at least part of process 1100 may be performed by the processing device 140 (implemented in, for example, the computing device 200 shown in FIG. 2). For example, the process 1100 may be stored in a storage device (e.g., the storage device 150, the storage 220, the storage 390) in the form of instructions (e.g., an application), and invoked and/or executed by the processing device 140 (e.g., the processor 210 illustrated in FIG. 2, the CPU 340 illustrated in FIG. 3, or one or more units in the processing device 140 illustrated in FIG. 4). The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In 1102, at least one medical image of an object may be obtained. The at least one medical image of the object may be obtained by the processing device 140 (e.g., the acquisition unit 410). In some embodiments, the object may be a patient or a portion of the patient. In some embodiments, the at least one medical image of the object may be a static medical image including a computed tomography (CT) image, a magnetic resonance (MR) image, an ultrasound image, or the like, or any combination thereof. For example, the at least one medical image may include reconstructed three-dimensional (3D) CT images of the object. The reconstructed 3D CT images of the object may be static 3D CT images which may indicate anatomical structure information of the object. As used herein, a static medical image refers to a medical image of an object or a portion thereof that does not undergo or is not affected by a physiological motion (e.g., cardiac motion, respiratory motion, muscular contraction and relaxation, etc.). It may be because that the object or a portion thereof is located far away from a source of a physiological motion. For instance, the head, an arm, or a leg of an object is considered not to undergo or be affected by the cardiac motion of the object. In some embodiments, the at least one medical image of the object may be generated by the apparatus 110 before the process 900, and stored in the storage device 150. In some embodiments, the generation of the at least one medical image of the object may also be referred to as a preoperative medical examination. In some embodiments, the processing device 140 may retrieve the at least one medical image of the object from the storage device 150 or the apparatus 110.

In 1104, one or more regions of interest in one or more (e.g., each) of the at least one medical image may be determined. The one or more regions of interest may be determined by the processing device 140 (e.g., the control unit 420). In some embodiments, the region(s) of interest may include a target region of the object that need to be processed (or treated) by a medical instrument during a medical procedure. In some embodiments, the region(s) of interest may also include one or more regions around the target region. The medical procedure may include a surgery (e.g., an (image-guided) intervention or a biopsy procedure). The medical instrument may include a biopsy needle. The target region may include an organ (e.g., a lung, a liver, a heart, etc.) or a portion thereof (e.g., a tumor, a nodule, bleeding spot, or the like, or any combination thereof). In some embodiments, the region(s) of interest may be determined based on one or more image segmentation algorithms. Exemplary image segmentation algorithms may include a threshold segmentation algorithm, a region growing algorithm, a watershed segmentation algorithm, a morphological segmentation algorithm, a statistics segmentation algorithm, or the like, or any combination thereof.

Merely by way of example, the at least one medical image may be a set of 3D CT reconstructed images of the chest of the object, and a liver of the object may have a nodule. Therefore, a biopsy procedure may need to be conducted on the nodule to diagnose whether the nodule is malignant. The target region may include the nodule of the liver. The region(s) of interest in the set of chest 3D CT reconstructed images may include the nodule, the liver, the ribs, a blood vessel in the vicinity of the nodule, etc. The region(s) of interest may be obtained by segmenting the set of chest 3D CT reconstructed images using one or more image segmentation algorithms illustrated elsewhere in the present disclosure. For instance, because the nodule may have greater gray values than that of the normal liver tissue, the nodule may be segmented from the liver based on the difference in gray values.

In 1106, a 3-dimensional (3D) image including a set of elements corresponding to the object may be generated. The 3D image may generated by the processing device 140 (e.g., the acquisition unit 410). In some embodiments, a 3D image may generated based on at least two images of the object (and/or the instrument). In some embodiments, the at least two images of the object may be captured (or generated) by at least two capture devices (e.g., the first capture device 161, the second capture device 162). In some embodiments, each capture device of the at least two capture devices may capture one of the at least two images. The at least two images may include at least one same region of the object and/or the table from different directions (or angles). In some embodiments, the at least two images of the object may be real scene images (or dynamic images, or videos) of the object from different view angles. For example, the first capture device 161 and the second capture device 162 may capture the images of the object from different view angles (e.g., 45 degrees on the upper left and 45 degrees on the upper right, respectively). In some embodiments, the at least two images may include 3D contour information (e.g., in the form of depth information) of the object. The 3D contour information may be used to reconstruct the 3D surface of the object. In some embodiments, the at least two capture devices may capture at least two videos (or dynamic images) of the object. The at least two images may be at least a portion of the frame images of the at least two videos (or dynamic images). In some embodiments, the at least two capture devices may automatically capture the images (or dynamic images, or videos) of the object during the medical procedure continuously, periodically, or aperiodically from time to time, and the images (or dynamic images, or videos) may be transmitted to the processing device 140 and/or the storage device 150 in real time, such that the processing device 140 may obtain the images (or dynamic images, or videos). In some embodiments, the processing device 140 may transmit instruction(s) for capturing images (or dynamic images, or videos) of the object to the capture devices, such that the capture devices may capture the images (or dynamic images, or videos) and transmit the images (or dynamic images, or videos) to the processing device 140.

In some embodiments, the 3D image may be a dynamic image (or video) reconstructed based on the at least two images (or dynamic images, or videos). The dynamic image may be generated by the processing device 140 (e.g., the reconstruction unit 440). In some embodiments, if the medical instrument is located close to the object, the instrument may be presented in the dynamic image. In some embodiments, the processing device 140 may reconstruct the 3D image based on one or more image reconstruction algorithms (e.g., a monocular vision algorithm, a stereo vision algorithm, a shape from shading algorithm, etc.). In some embodiments, the processing device 140 (e.g., the registration unit 430) may register the at least two images before reconstructing the 3D image based on the at least two images. In some embodiments, the processing device 140 (e.g., the registration unit 430) may register the at least two images (or a portion thereof) using one or more image registration algorithms (e.g., a grayscale and template based registration algorithm, a feature based registration algorithm, a domain transformation based registration algorithm, etc.). In some embodiments, the processing device 140 may pre-process the at least two images before registering the at least two images. Exemplary pre-processing may include denoising, image enhancing, image segmentation, etc. In some embodiments, the processing device 140 may register each image frame of the video captured by the first capture device 161 with an image frame of the video captured by the second capture device 162, and generate the dynamic image (or video).

In some embodiments, the 3D image may include a set of elements corresponding to the object. In some embodiments, the 3D image may be a reconstructed 3D dynamic image (or a reconstructed 3D video) of the object. In some embodiments, the processing device 140 may process the reconstructed 3D dynamic image (or 3D video) of the object. For example, the processing device 140 may segment the reconstructed 3D dynamic image (or 3D video) so that in the reconstructed 3D dynamic image or the reconstructed 3D video, the object may be extracted from the background (e.g., the table). In some embodiments, a contoured surface (or profile) the object may be highlighted. In some embodiments, the set of elements corresponding to the contoured surface (or profile) of the object may change (e.g., periodically) with the motion of the object.

In 1108, an AR image may be generated by projecting at least one of the one or more regions of interest in the at least one medical image onto the dynamic image. In some embodiments, the at least one of the one or more regions of interest may include the target region of the object. In some embodiments, the AR image may present a real scene of the object (or a portion thereof), the at least one of the one or more regions of interest, and/or a real scene of the instrument, etc. The AR image may be generated by the processing device 140 (e.g., the projection unit 450). In some embodiments, the AR image may be a 3D dynamic AR image or a 3D AR video of the object. In this situation, the at least one medical image may be a static medical image, which may be projected onto each frame of the dynamic image to generate the 3D dynamic AR image. Thus, in the generated 3D dynamic AR image, the target region of the object may appear to be stationary which may be easy to identify for guide the operation of the instrument. In some embodiments, the processing device 140 may identify the at least one of the one or more regions of interest in the at least one of medical image to be projected, and then project it onto the 3D image generated in operation 908 to generate the AR image. In some embodiments, the processing device 140 may identify the at least one of the one or more regions of interest (e.g., the target region of the object) in the at least one medical reconstructed images to be projected based on one or more instructions of the operator. For example, the operator may select the at least one of the one or more regions of interest to be projected through a user interface implemented on the terminal 130, and the terminal 130 may send corresponding instructions to the processing device 140. In some embodiments, the processing device 140 (e.g., the registration unit 430) may register the at least one of the one or more regions of interest and the dynamic image in space. In some embodiments, the processing device 140 may fuse the at least one of the one or more regions of interest and the 3D image to generate the AR image.

In 1110, the AR image may be provided for guiding an operation of the instrument. As described above, the AR image may include the at least one of the one or more regions of interest. In some embodiments, the processing device 140 (e.g., the display unit 460) may display the AR image on a display device and/or on a portion of the instrument (e.g., the table on which the object is supported). More descriptions of the display device may be found elsewhere in the present disclosure (e.g., FIG. 5 and the descriptions thereof). In some embodiments, the operator may view the AR image from the display device. In some embodiments, the operator may adjust a display effect of the AR image. For example, the operator may choose to zoom in or out, and/or drag the AR image, so that the operator may view different portions (or scopes) of the object with different amplifications. The processing device 140 may receive instruction(s) associated with the display effect of the AR image from the operator and perform corresponding zooming in or out and/or dragging operations, or the like, to realize the display effect. In some embodiments, the operator may select or change the at least one of the one or more regions of interest to be projected onto the 3D image, and accordingly, the processing device 140 may receive one or more instructions for selecting or changing the at least one of the one or more regions of interest to be projected onto the 3D image and perform corresponding adjustment(s) in the AR image. In some embodiments, during the procedure, the operator may locate the at least one of the one or more regions of interest according to the AR image, and perform operation(s) of the instrument (e.g., biopsy needle). For example, the operator may observe, based on the AR image, in real time, whether an insertion position of the biopsy needle is close to the target region of the object, whether the needling direction (or puncture angle) is proper, and/or whether the puncture depth is proper, etc.

In some embodiments, the processing device 140 may automatically identify the target region of the object in the AR image based on one or more preset parameters (e.g., a puncture location) associated with the procedure. For example, if the procedure targets a lung nodule, the processing device 140 may automatically identify the target region of the object in which the lung nodule is located by segmenting the AR image (e.g., the at least one of the one or more regions of interest projected onto the 3D image). In some embodiments, the processing device 140 may automatically determine a target position in the object for operating the medical instrument based on the positions of the elements (e.g., pixels or voxels) corresponding to the segmented target region of the object in the AR image. For example, the processing device 140 may determine a center position of the lung nodule as the target position. In some embodiments, the processing device 140 may determine a current puncture location of the biopsy needle, a current puncture angle of the biopsy needle, a current puncture depth of the biopsy needle, an offset between the target position in the object and the current puncture location of the biopsy needle, etc., based on the AR image. In some embodiments, the processing device 140 may display the information relating to the locations associated with the target region and the biopsy needle in the display device for the operator's reference, and guide the operation of the biopsy needle.

It should be noted that the above description of the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the process 1100 may further include operations for generating control instructions, and/or transmitting the control instructions to the control unit 420 for generating one or more notifications to guide the operation of the medical instrument. As another example, after (or during) the instrument is operated according to the guidance of the AR image, a postoperative (or intraoperative) examination (e.g., an imaging process) may be performed to inspect the position of the medical instrument relative to the target region of the object.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device including a storage device and at least one processor for positioning an object positioned on a table, the method comprising:
    obtaining a plan image, the plan image illustrating a virtual surface of the object and a virtual surface of the table;
    determining a target position of the table based on the virtual surface of the table;
    obtaining, by one or more capture devices, a 3-dimensional (3D) image, the 3D image including a first set of elements corresponding to the object and a second set of elements corresponding to the table;
    generating an augmented reality image by projecting the virtual surface of the table onto the 3D image;
    displaying the augmented reality image on a display device;
    determining a current position of the table based on the 3D image; and
    causing the table to move based on the current position and the target position of the table.

2. The method of claim 1, wherein the display device is a head mounted display (HMD) or a panel display.

3. The method of claim 1, wherein the obtaining the plan image comprises:
    obtaining the plan image based on one or more tomography images of the object.

4. The method of claim 1, wherein the 3D image is a synthetic 3D optical image generated based on at least two images of the object acquired by at least two capture devices.

5. The method of claim 1, wherein at least one of the one or more capture devices is a depth camera.

6. The method of claim 1, wherein at least one of the one or more capture devices is fixed above the object and the table, and the one or more capture devices are configured to capture the object and the table from one or more directions.

7. The method of claim 1, wherein the plan image includes a plurality of elements, and each of the plurality of elements has a coordinate in a digital imaging and communications in medicine (DICOM) coordinate system or an international electrotechnical commission (IEC) coordinate system.

8. The method of claim 1, wherein each element of the 3D image has a coordinate in a digital imaging and communications in medicine (DICOM) coordinate system or an international electrotechnical commission (IEC) coordinate system.

9. The method of claim 1, wherein the causing the table to move comprises:
determining a first offset between the current position of the table and the target position of the table;
determining whether the table needs to be moved based on the first offset; and
in response to a determination that the table needs to be moved, causing the table to move to the target position of the table based on the first offset.

10. The method of claim 9, wherein the causing the table to move comprises:
providing the first offset to an operator;
receiving, from the operator, one or more instructions for moving the table; and
causing the table to move to the target position of the table according to the one or more instructions.

11. The method of claim 1, further comprising:
generating a second augmented reality image by projecting the virtual surface of the object onto the 3D image; and
displaying the second augmented reality image on the display device.

12. The method of claim 11, further comprising:
receiving, from an operator, one or more instructions for moving the object; and
causing the object to move according to the one or more instructions.

13. The method of claim 1, further comprising:
obtaining at least one medical image of the object;
determining one or more regions of interest in the at least one medical image;
generating a third augmented reality image by projecting at least one of the one or more regions of interest in the at least one medical image onto the 3D image; and
providing the third augmented reality image for guiding an operation of a medical instrument.

14. The method of claim 13, wherein the at least one medical image includes a set of medical images of the object, the 3D image includes a dynamic 3D image, and the third augmented reality image includes a dynamic augmented reality image.

15. The method of claim 14, wherein the generating the third augmented reality image by projecting the at least one of the one or more regions of interest in the at least one medical image onto the 3D image comprises:
obtaining a first waveform of a motion generated during a first time period;
acquiring a second waveform of the motion generated during a second time period;
determining a first reference phase in the first waveform and a second reference phase in the second waveform;
projecting the at least one of the one or more regions of interest in a first medical image of the set of medical images onto a first frame of the dynamic 3D image, the first medical image being generated at a first time point corresponding to the first reference phase, the first frame of the dynamic 3D image being generated at a second time point corresponding to the second reference phase.

16. The method of claim 15, further comprising:
projecting the at least one of the one or more regions of interest in a second medical image of the set of medical images onto a second frame of the dynamic 3D image, the second medical image being generated at a third time point corresponding to a third phase, the second frame of the dynamic 3D image being generated at a fourth time point corresponding to a fourth phase, a phase difference between the first time point and the third time point is the same as a phase difference between the second time point and the fourth time point.

17. The method of claim 1, wherein the causing the table to move based on the current position and the target position of the table comprises:
obtaining a registration result by registering the 3D image with the plan image;
determining a first offset between a first position of the object in the 3D image and a second position of the object in the plan image based on the registration result;
determining that the first offset is equal to a second offset between a third position of the table in the 3D image and a fourth position of the table in the plan image if a first relative distance between the object and the table in the plan image is deemed to be equal to a second relative distance between the object and the table in the 3D image; and
determining whether the table needs to be moved by comparing the second offset with a threshold.

18. The method of claim 17, further comprises:
in response to determining that the first relative distance is not equal to the second relative distance,
determining the second offset based on the first offset between the first position of the object and the second position of the object, the first relative distance, and the second relative distance; and
causing the table to move based on the second offset.

19. A system for positioning an object positioned on a table, comprising:
at least one storage device including a set of instructions or programs; and
at least one processor configured to communicate with the at least one storage device, wherein when executing the set of instructions or programs, the at least one processor is configured to cause the system to perform operations including:
obtaining a plan image, the plan image illustrating a virtual surface of the object and a virtual surface of the table;
determining a target position of the table based on the virtual surface of the table;
obtaining, by one or more capture devices, a 3-dimensional (3D) image, the 3D image including a first set of elements corresponding to the object and a second set of elements corresponding to the table;
generating an augmented reality image by projecting the virtual surface of the table onto the 3D image;
displaying the augmented reality image on a display device;
determining a current position of the table based on the 3D image; and
causing the table to move based on the current position and the target position of the table.

20. A non-transitory computer readable medium storing instructions, the instructions, when executed by at least one processor, causing the at least one processor to implement a method comprising:
obtaining a plan image, the plan image illustrating a virtual surface of the object and a virtual surface of the table;
determining a target position of the table based on the virtual surface of the table;

obtaining, by one or more capture devices, a 3-dimensional (3D) image, the 3D image including a first set of elements corresponding to the object and a second set of elements corresponding to the table;
generating an augmented reality image by projecting the virtual surface of the table onto the 3D image;
displaying the augmented reality image on a display device;
determining a current position of the table based on the 3D image; and
causing the table to move based on the current position and the target position of the table.

* * * * *